US008787526B2

(12) United States Patent
Hyde et al.

(10) Patent No.: US 8,787,526 B2
(45) Date of Patent: Jul. 22, 2014

(54) SYSTEMS, DEVICES, AND METHODS INCLUDING IMPLANTS FOR MANAGING CUMULATIVE X-RAY RADIATION DOSAGE INCLUDING X-RAY RADIATION DIRECTION DETERMINATION DEVICES

(75) Inventors: Roderick A. Hyde, Redmond, WA (US); Muriel Y. Ishikawa, Livermore, CA (US); Eric C. Leuthardt, St. Louis, MO (US); Michael A. Smith, Phoenix, AZ (US); Elizabeth A. Sweeney, Seattle, WA (US); Lowell L. Wood, Jr., Bellevue, WA (US)

(73) Assignee: Elwha LLC

( * ) Notice: Subject to any disclaimer, the term of this patent is extended or adjusted under 35 U.S.C. 154(b) by 414 days.

(21) Appl. No.: 13/373,678

(22) Filed: Nov. 23, 2011

(65) Prior Publication Data

US 2013/0062527 A1    Mar. 14, 2013

Related U.S. Application Data

(63) Continuation-in-part of application No. 13/199,836, filed on Sep. 8, 2011.

(51) Int. Cl.
*H05G 1/42* (2006.01)
(52) U.S. Cl.
USPC ............................... 378/97; 378/98.8; 378/65
(58) Field of Classification Search
USPC ................. 378/65, 97, 98.8, 108; 250/370.07
See application file for complete search history.

(56) References Cited

U.S. PATENT DOCUMENTS

| 5,833,603 | A  | 11/1998 | Kovacs et al. |
| 6,398,710 | B1 | 6/2002  | Ishikawa et al. |
| 6,431,175 | B1 | 8/2002  | Penner et al. |
| 7,119,676 | B1 | 10/2006 | Silverstrim et al. |
| 7,778,692 | B2 | 8/2010  | Scarantino et al. |
| 2002/0137991 | A1 | 9/2002 | Scarantino et al. |
| 2003/0125616 | A1 | 7/2003 | Black et al. |
| 2004/0211917 | A1 | 10/2004 | Adamovics |
| 2006/0093088 | A1 | 5/2006 | Sowerby et al. |
| 2007/0063154 | A1 | 3/2007 | Chen et al. |
| 2007/0164223 | A1 | 7/2007 | Hennessy et al. |
| 2008/0154086 | A1 | 6/2008 | Stubbs |
| 2008/0212737 | A1 | 9/2008 | D'Souza et al. |
| 2008/0312712 | A1 | 12/2008 | Penner |
| 2009/0018403 | A1 | 1/2009 | Black et al. |
| 2009/0121144 | A1 | 5/2009 | Black et al. |
| 2009/0171404 | A1 | 7/2009 | Irani et al. |
| 2009/0228058 | A1 | 9/2009 | Daum et al. |
| 2009/0234672 | A1 | 9/2009 | Dicks et al. |
| 2010/0051820 | A1 | 3/2010 | Okada |
| 2010/0152644 | A1 | 6/2010 | Pesach et al. |
| 2010/0161004 | A1 | 6/2010 | Najafi et al. |
| 2011/0130800 | A1 | 6/2011 | Weinstein et al. |
| 2011/0301441 | A1 | 12/2011 | Bandic et al. |
| 2011/0309945 | A1 | 12/2011 | Hyde et al. |

OTHER PUBLICATIONS

Jirasek et al.; "How Does the Chemistry of Polymer Gel Dosimeters Affect their Performance?"; 5th International Conference of Radiotherapy Gel Dosimetry, Journal of Physics: Conference Series 164; bearing a date of Sep. 11, 2011 and 2009; pp. 1-13 plus cover page; vol. 164; IOP Publishing Ltd.

(Continued)

*Primary Examiner* — Courtney Thomas

(57) ABSTRACT

Systems, devices, and methods are described including implantable radiation sensing devices having exposure determination devices that determines exposure information based on the at least one in vivo measurand output.

31 Claims, 10 Drawing Sheets

(56) References Cited

OTHER PUBLICATIONS

McAuley et al.; "Fundamentals of Polymer Gel Dosimeters"; Institute of Physics Publishing, Journal of Physics: Conference Series 56, Third International Conference on Radiotherapy Gel Dosimetry; printed on Nov. 22, 2011 and bearing a date of 2006; pp. 35-44; vol. 56; IOP Publishing Ltd.

Schreiner et al.; "Review of Fricke Gel Dosimeters"; Journal of Physics: Conference Series 3, Third International Conference on Radiotherapy Gel Dosimetry; bearing a date of Sep. 11, 2011 and 2004; pp. 9-21 plus cover page; vol. 3; IOP Publishing Ltd.

PCT International Search Report; International App. No. PCT/US2012/054101; bearing a date of Nov. 16, 2012; pp. 1-2.

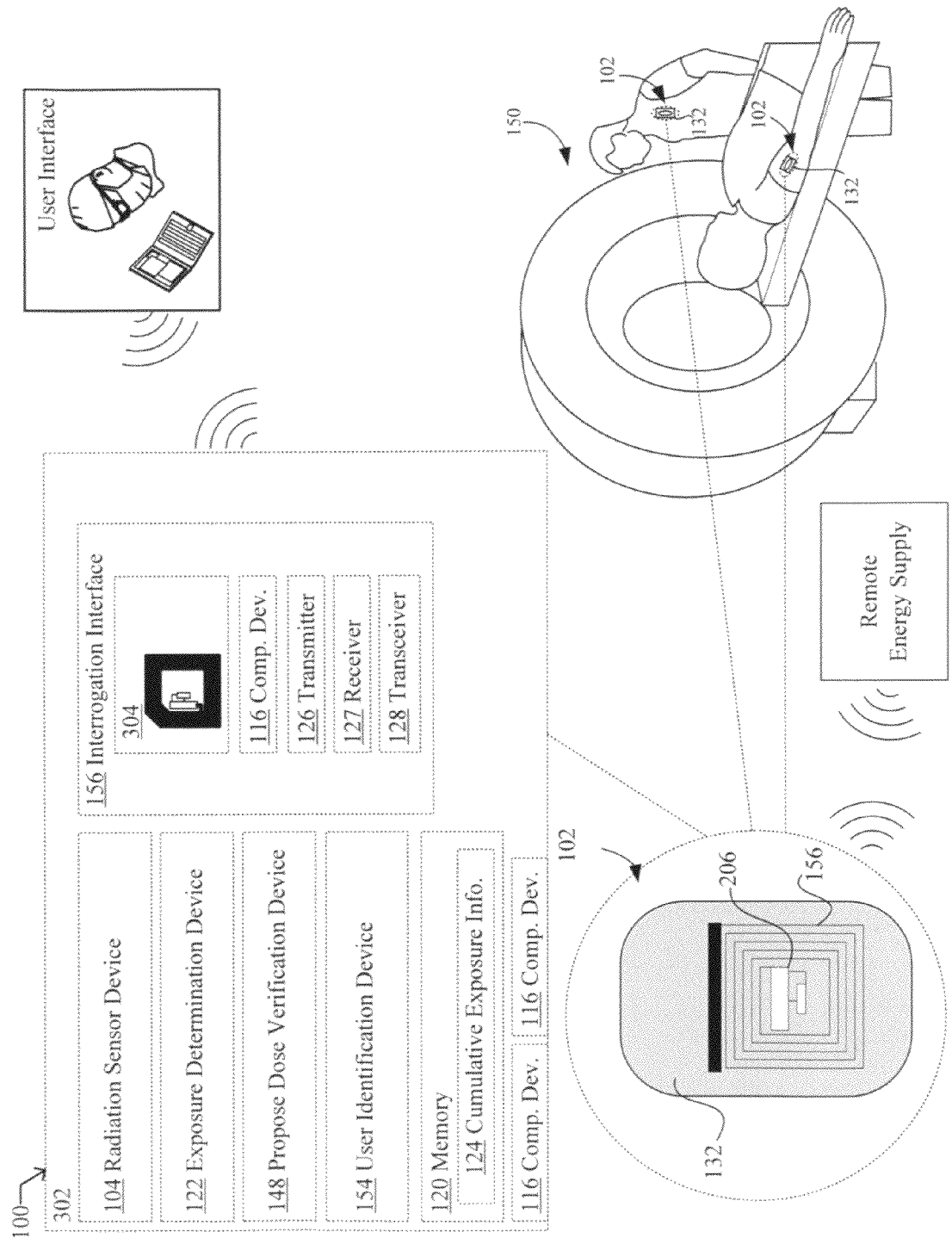

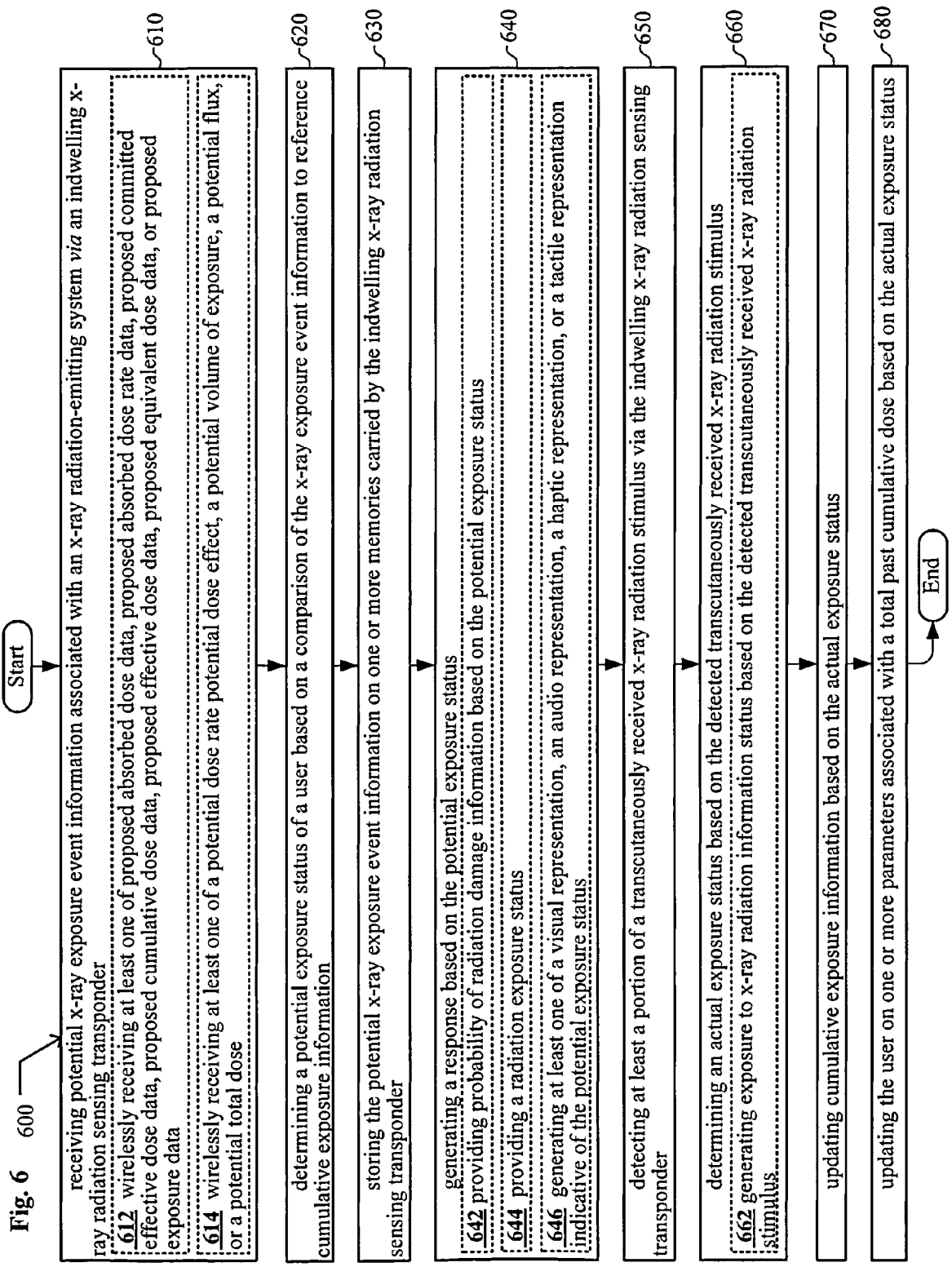

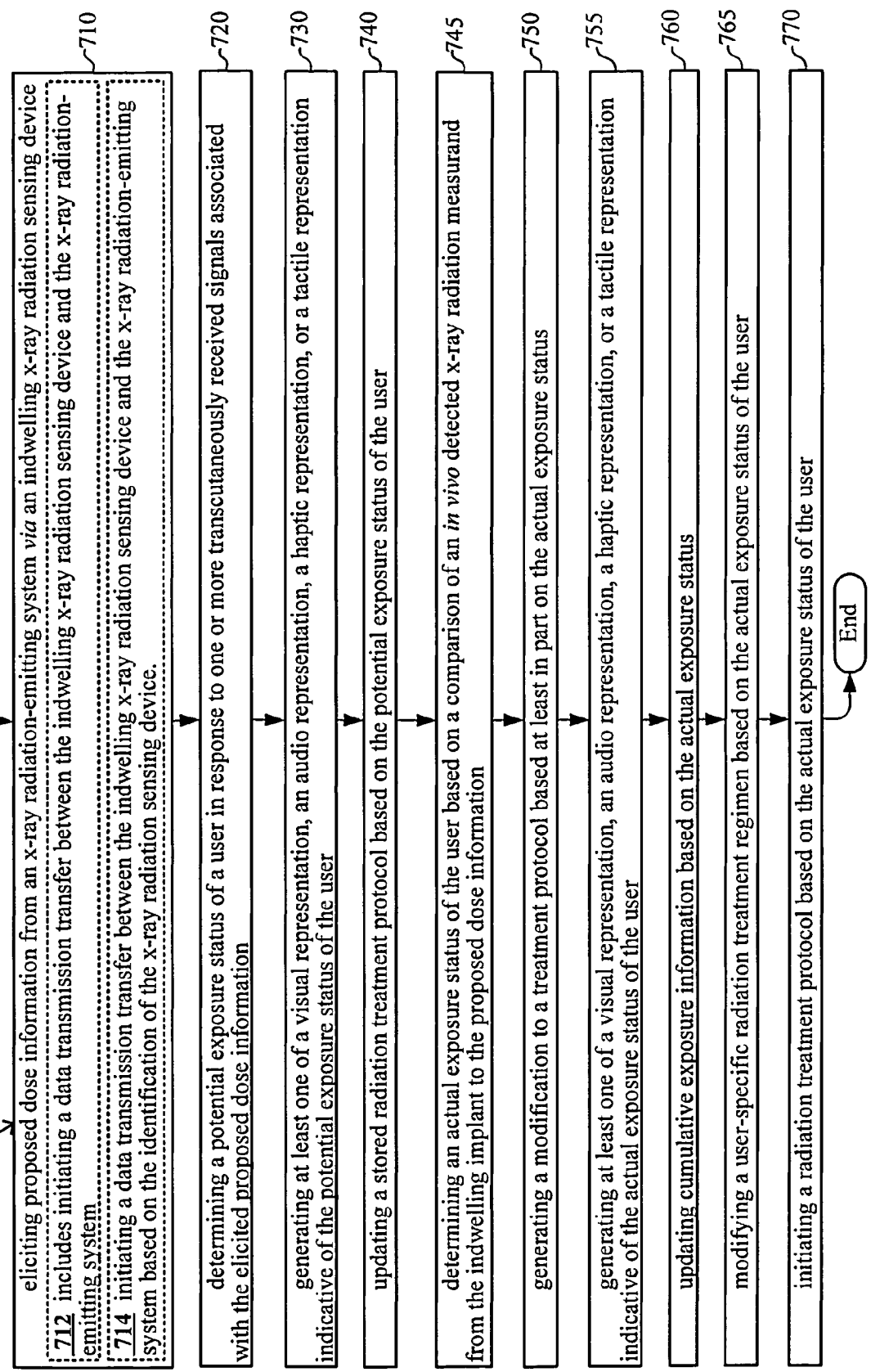

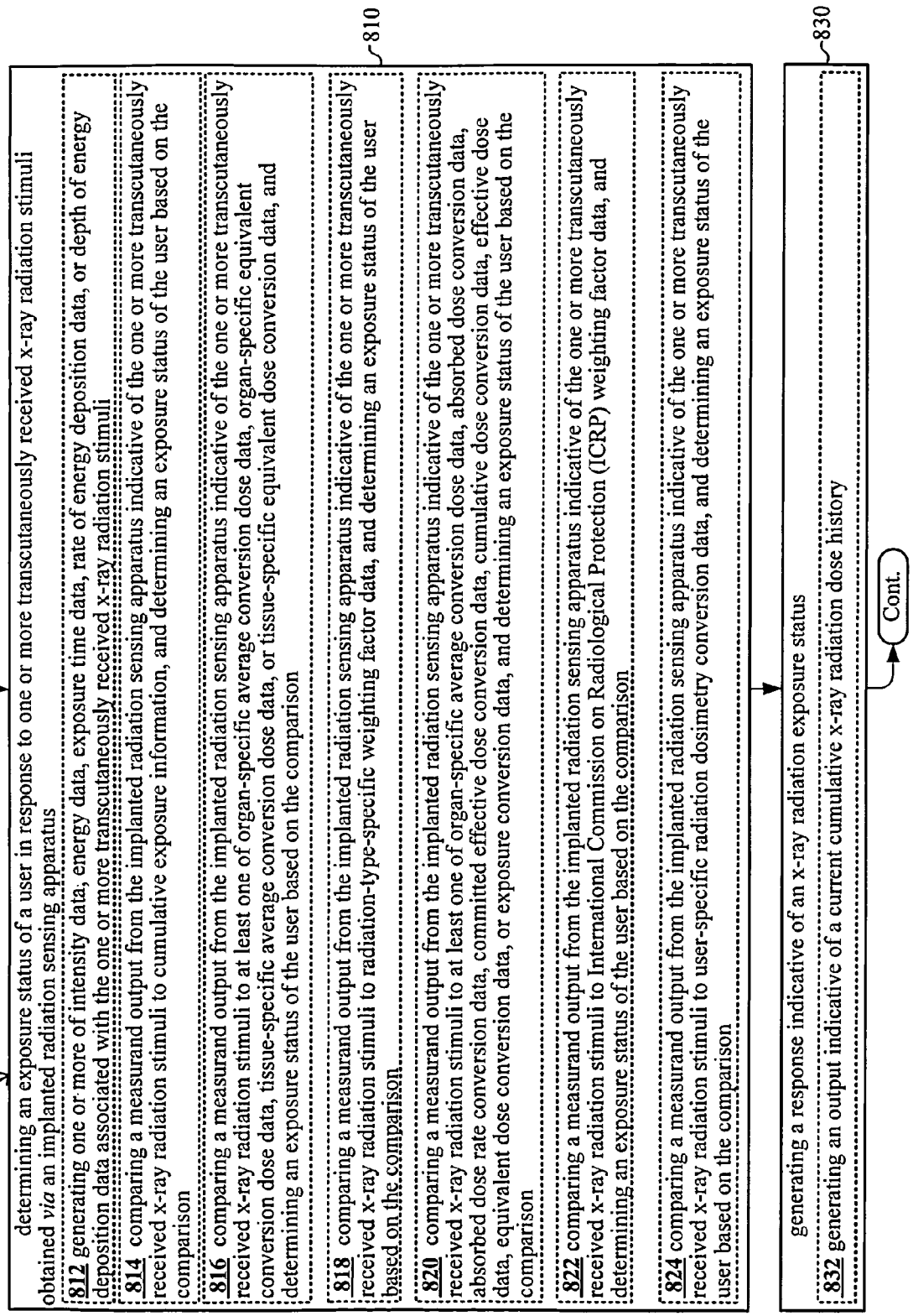

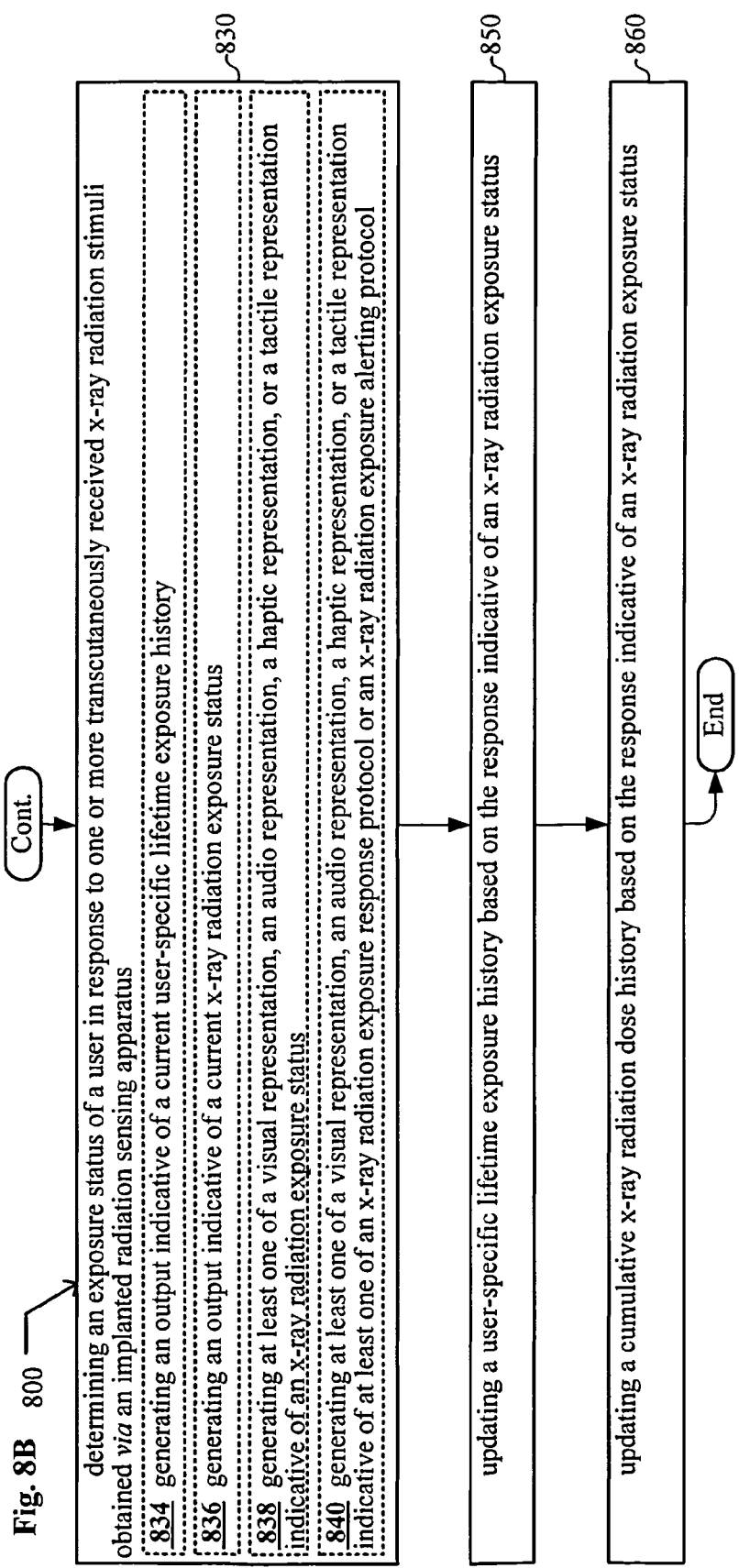

SYSTEMS, DEVICES, AND METHODS INCLUDING IMPLANTS FOR MANAGING CUMULATIVE X-RAY RADIATION DOSAGE INCLUDING X-RAY RADIATION DIRECTION DETERMINATION DEVICES

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the United States Patent and Trademark Office (USPTO) extra-statutory requirements, the present application constitutes a continuation-in-part of U.S. patent application Ser. No. 13/199,836, titled SYSTEMS, DEVICES, AND METHODS INCLUDING IMPLANTS FOR MANAGING CUMULATIVE X-RAY RADIATION DOSAGE, naming Roderick A. Hyde, Muriel Y. Ishikawa, Eric C. Leuthardt, Michael A. Smith, Elizabeth A. Sweeney, Lowell L. Wood, Jr. as inventors, filed 8, Sep. 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In an aspect, the present disclosure is directed to, among other things, an implantable radiation sensing device including an x-ray radiation sensor device and an x-ray radiation direction-determination device. In an embodiment, the implantable radiation sensing device includes an x-ray radiation sensor device operable to detect, in vivo, one or more x-ray radiation stimuli associated with an x-ray radiation exposure event. In an embodiment, the x-ray radiation sensor device includes at least a first direction-selective sensor for detecting, in vivo, one or more x-ray radiation stimuli propagating in a first direction, and a second direction-selective sensor for detecting, in vivo, one or more x-ray radiation stimuli propagating in a second direction. In an embodiment, the second direction differs from the first direction. In an embodiment, the implantable radiation sensing device includes an x-ray radiation direction-determination device operable to determine at least one of an x-ray radiation source location or an x-ray radiation propagation direction based on one or more measurand outputs from the first direction-selective sensor or the second direction-selective sensor.

In an aspect, the present disclosure is directed to, among other things, an x-ray radiation sensor device including a multi-pixel x-ray radiation sensor and an exposure determination device. In an embodiment, the x-ray radiation sensor device includes a multi-pixel x-ray radiation sensor having at least a first pixel and a second pixel. In an embodiment, the second pixel includes one or more x-ray mass attenuation coefficients or mass energy-absorption coefficients different from the first pixel, the multi-pixel x-ray radiation sensor operable to generate one or more measurand outputs associated with an in vivo detected x-ray radiation exposure event. In an embodiment, the x-ray radiation sensor device includes an exposure determination device that determines exposure information based on the one or more measurand outputs from the multi-pixel x-ray radiation sensor.

In an aspect, the present disclosure is directed to, among other things, an implantable radiation sensing device including an x-ray radiation sensor device operable to detect, in vivo, one or more x-ray radiation stimuli associated with an x-ray radiation exposure event and to generate one or more measurand outputs. In an embodiment, the x-ray radiation sensor device includes one or more gel dosimeters In an embodiment, the one or more gel dosimeters include at least one polymer gel dosimeter. In an embodiment, the one or more gel dosimeters include at least one 2-hydroxyethyl-acrylate-based gel dosimeter or 2-hydroxyethyl methacrylate-based gel dosimeter. In an embodiment, the one or more gel dosimeters include at least one polymethacrylic acid-based gel dosimeter or polyacrylamide-based gel dosimeter. In an embodiment, the one or more gel dosimeters include at least one Fricke gel dosimeter. In an embodiment, the one or more gel dosimeters include at least one polyvinyl alcohol-Fricke-based gel dosimeter. In an embodiment, the one or more gel dosimeters include at least one hydrogel-based gel dosimeter or cryogel-based gel dosimeter. In an embodiment, the implantable radiation sensing device includes an exposure determination device including one or more computing devices that determine a spatial dose distribution associated with the x-ray radiation exposure event based on the one or more measurand outputs from the x-ray radiation sensor device.

BRIEF DESCRIPTION OF THE FIGURES

FIG. 3A is a perspective view of a system according to one embodiment.

FIG. 6 shows a flow diagram of a method according to one embodiment.

FIG. 7 shows a flow diagram of a method according to one embodiment.

FIGS. 8A and 8B show a flow diagram of a method according to one embodiment.

DETAILED DESCRIPTION

Figure 1:
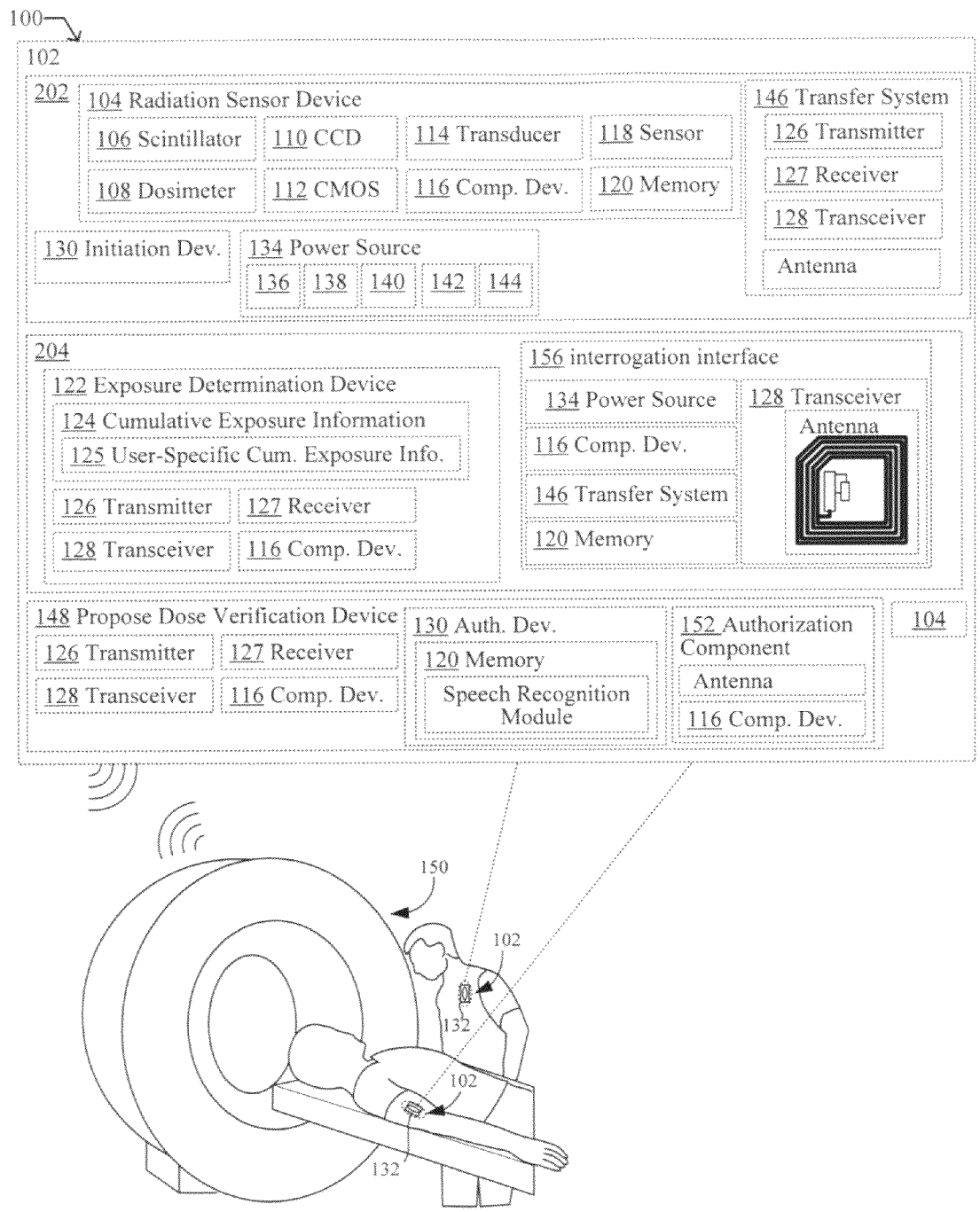
FIG. 1 is a perspective view of a system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Medical systems (e.g., fluoroscopy systems, computed tomography systems, radiography systems, radiation treatment systems, x-ray imaging system, etc.) are valuable diagnostics and treatment tools in medical practice. Likewise, cabinet x-ray systems (e.g., closed x-ray systems, x-ray inspection systems, x-ray screening systems, x-ray security systems, baggage x-ray systems, etc.) are useful tools for detection of contraband, contaminants, or manufacturing defects without damaging or destroying the item being examined.

Exposure to radiation may cause cancer (especially leukemia), birth defects in the children of exposed parents and cataracts. These health effects (excluding genetic effects) have been observed in studies of medical radiologists, uranium miners, radium workers, and radiotherapy patients who have received large doses of radiation. Studies of radiation effects on laboratory animals have provided a large body of data on radiation health effects including genetic effects. Most of the studies mentioned above involve acute exposure to high levels of radiation. Acute exposure can be, for example, exposure to hundreds of rem (Roentgen equivalent in man) within a few hours or less. Such radiation doses far exceed the occupational dose limits currently recommended (less than 5 rem per year). However, the major concerns today are about delayed health effects arising from chronic cumulative exposure to radiation.

The major health concern from chronic cumulative exposure to radiation is cancer which may appear 5 to 20 years after exposure to relatively low levels of radiation. The current limits for radiation exposure set by the FDA for adults are: 50 mSv (millisieverts) (5 rems) per year and 30 mSv (3 rems) per single dose. (http://tech.mit.edu/Bulletins/Radiation/rad5.txt). For children, who are more vulnerable to radiation, the limits are 5 mSv (0.5 rems) annually and 3 mSv (0.3 rems) per single dose. A lifetime occupational exposure level of no greater than 400 mSv (40 rems) is recommended by government agencies (Hall et al., Canadian Fam. Physician 52: 976-77, 2006). Compliance with these radiation exposure limits is complicated by the lack of cumulative radiation exposure data, especially in regard to lifetime exposure limits. Also the increased usage of computed tomography scans for medical imaging (Brenner and Hall, N. Engl. J. Med. 357: 2277-84, 2007) has created a need for monitoring and recording radiation exposure data to avoid exceeding exposure limits.

FIG. 1 shows an implantable radiation sensing device 102, in which one or more methodologies or technologies can be implemented such as, for example, detecting an x-ray radiation stimulus in vivo, monitoring lifetime x-ray radiation exposure, assessing a radiation exposure status, generating (e.g., calculating, evaluating, determining, gauging, quantifying, resolving, or the like) exposure information, transcutaneously transmitting x-ray radiation dose information, receiving potential x-ray exposure event information associated with an x-ray radiation-emitting system, determining a potential exposure status of a user, eliciting proposed dose information from an x-ray radiation-emitting system or the like. In an embodiment, during operation, the implantable radiation sensing device 102 detects x-ray radiation exposure events while implanted within a biological subject (e.g., patient, user, non-human biological subject, human biological subject, etc).

In an embodiment, the radiation sensing device 102 includes one or more x-ray radiation sensor devices 104. In an embodiment, the one or more x-radiation sensing devices 102 are operable to detect (e.g., assess, calculate, evaluate, determine, gauge, measure, monitor, quantify, resolve, sense, or the like) an incident x-ray radiation, in vivo. In an embodiment, the radiation sensing device 102 is operable to detect at least one characteristic (e.g., a fundamental characteristic, a spectral characteristic, a spectral signature, a physical quantity, an absorption coefficient, or the like) associated with an x-ray radiation exposure event, while implanted in a biological subject.

Non-limiting examples of x-ray radiation sensor devices 104 include scintillators 106 (e.g., inorganic scintillators, thallium doped cesium iodide scintillators, scintillator-photodiode pairs, scintillation detection devices, etc.), dosimeters 108 (e.g., x-ray dosimeters, thermoluminescent dosimeters, etc.), optically stimulated luminescence detectors, photodiode arrays, charge-coupled devices (CCDs) 110, complementary metal-oxide-semiconductor (CMOS) devices 112, or the like. In an embodiment, the x-ray radiation sensor device 104 includes one or more x-ray radiation fluoroscopic elements. In an embodiment, the x-ray radiation sensor device 104 includes one or more phosphorus doped elements (e.g., ZnCdS:Ag phosphorus doped elements). In an embodiment, the x-ray radiation sensor device 104 includes one or more amorphous silicon thin-film transistor arrays. In an embodiment, the x-ray radiation sensor device 104 includes one or more phosphors.

In an embodiment, the x-ray radiation sensor device 104 includes one or more transducers 114 that detect and convert x-rays into electronic signals. For example, in an embodiment, the x-ray radiation sensor device 104 includes one or more x-ray radiation scintillation crystals. In an embodiment, the x-ray radiation sensor device 104 includes one or more thallium doped cesium iodide crystals (e.g., cesium iodide crystals doped with thallium CsI(Tl)). In an embodiment, the x-ray radiation sensor device 104 includes a computing device 116 that processes the electronic signals generated by the one or more transducers 114 to determine one or more of intensity, energy, time of exposure, date of exposure, exposure duration, rate of energy deposition, depth of energy deposition, or the like associated with each x-ray detected. In an embodiment, during operation, incident x-ray radiation interacts with one or more detector crystalline materials (e.g., cadmium zinc telluride, etc.) within the x-ray radiation sensor device 104, which results in the generation of a current indicative of, for example, the energy of the incident x-ray radiation.

In an embodiment, the radiation sensing device 102 includes circuitry configured to, for example, detect x-ray radiation, determine a cumulative exposure information based on the at least one measurand, or the like. For example, in an embodiment, the x-ray radiation sensor device 104 includes at least one computing device 116 operably coupled to one or more sensors 118 that measure at least one of intensity data, energy, exposure time, rate of energy deposition, or depth of energy deposition associated with an x-ray radiation stimulus. In an embodiment, the x-ray radiation sensor device 104 includes at least one of a photodiode array, a scintillator, a thermoluminescent dosimeter, an x-ray radiation fluoroscopic element, or an amorphous silicon thin-film transistor array (e.g., amorphous silicon, thin-film transistor, active matrix array, etc.) operably coupled to at least one computing device 116. In an embodiment, the radiation sensing device 102 includes an x-ray radiation sensor device 104 having one or more pixels that acquire at least a portion of a transcutaneous x-ray radiation stimulus and transduces the x-ray radiation stimulus acquired by the x-ray radiation sensor device 104 into at least one measurand indicative of an x-ray radiation exposure during an integration period of the x-ray radiation sensor device 104.

In an embodiment, circuitry includes, among other things, one or more computing devices 116 such as a processor (e.g., a microprocessor), a central processing unit (CPU), a digital signal processor (DSP), an application-specific integrated circuit (ASIC), a field programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In some embodiments the computing device 116 is a server. In some embodiments the computing device 116 is a distributed-core processor. In some embodiments the computing device 116 is a single processor that is part of a single computing system. In some embodiments the computing device 116 is a multiple processors distributed over one or many computing system, which may or may not be configured to work together. In an embodiment, the computing device 116 is configured to execute computer readable instructions in order to execute one or more operations described herein, and as illustrated in FIGS. 4-8B.

In an embodiment, the radiation sensing device 102 includes circuitry having one or more components operably coupled (e.g., communicatively, electromagnetically, magnetically, ultrasonically, optically, inductively, electrically, capacitively coupled, or the like) to each other. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices 120 that, for example, store instructions or data. Non-limiting examples of one or more memory devices 116 include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices 120 include Erasable Programmable Read-Only Memory (EPROM), flash memory, or the like. The one or more memory devices 120 can be coupled to, for example, one or more computing devices 116 by one or more instructions, data, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operably coupled to at least one computing device 116 to control (electrical, electromechanical, software-implemented, firmware-implemented, or other control, or combinations thereof) at least one parameter associated with, for example, determining an exposure status of a user in response to one or more transcutaneously received x-ray radiation stimuli obtained via the implantable radiation sensing device 102.

In an embodiment, circuitry includes a computer-readable media drive or memory slot can be configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, the radiation sensing device 102 includes circuitry having one or more modules optionally operable for communication with one or more input/output components that are configured to relay user output and/or input. In an embodiment, a module includes one or more instances of electrical, electromechanical, software-implemented, firmware-implemented, or other control devices. Such devices include one or more instances of memory 120; computing devices 116; antennas; power or other supplies; logic modules or other signaling modules; gauges or other such active or passive detection components; piezoelectric transducers, shape memory elements, micro-electro-mechanical system (MEMS) elements, or other actuators.

In an embodiment, the implantable radiation sensing device 102 shares, communicates etc., for example, radiation exposure information with a network (e.g., a computer network, a body area network, a wireless area network, a smart room network, smart house network, a medical enterprise network, or the like). In an embodiment, the implantable radiation sensing device 102 communicates wirelessly with a computer network such as an institutional medical computer network, e.g. to access (read or write) electronic medical records e.g., for the patient or a population or to access information on the radiation source.

In an embodiment, the implantable radiation sensing device 102 is operably coupled to one or more sensors 118 (e.g., x-ray radiation sensors, body sensor units, etc.) via a communication network, a body area network (BAN), a body sensor network (BAN), a wireless body area network (WBAN), or the like. In an embodiment, the one or more sensors 118 form part of a body area network (BAN), a body sensor network (BAN), or a wireless body area networks (WBAN).

In an embodiment, the implantable radiation sensing device 102 communicates with a body area network or body sensor network, e.g., to identify a location of an area of exposure or location of the x-ray radiation source, or the like. In an embodiment, the implantable radiation sensing device 102 communicates with a body area network or body sensor network to interface with sensors 118 e.g., to assess effects of the dose, radiation exposure event, or the like. In an embodiment, the implantable radiation sensing device 102 is configure to communicate, via a wireless area network (e.g., a wireless personal area network, a wireless smart house network, a wireless area sensor network, or the like) to, e.g., access data regarding global positioning of the person or positional, area-wide radiation levels data, or other information on radiation source.

In an embodiment, the radiation sensing device 102 includes an exposure determination device 122. In an embodiment, the exposure determination device 122 is configured to determine cumulative exposure information 124 (e.g., cumulative x-ray radiation dose history data, lifetime exposure history data, x-ray radiation exposure alerting protocol data, x-ray radiation exposure response protocol data, x-ray radiation exposure status data, user-specific cumulative x-ray radiation dose history data, user-specific lifetime exposure history data, user-specific x-ray radiation exposure alerting protocol data, user-specific x-ray radiation exposure response protocol data, user-specific x-ray radiation exposure status data, user-specific cumulative exposure information 125, or the like) based on one or more measurand outputs. For example, in an embodiment, during operation, the implantable radiation sensing device 102 detects x-ray radiation exposure events while implanted within a biological subject and the exposure determination device 122 determines absorbed dose data based on one or more measurand outputs from the x-ray radiation sensor device 104. In an embodiment, absorbed dose data is communicated to an ex vivo input/output device, user interface, display, or the like.

In an embodiment, the exposure determination device 122 determines absorbed dose data based on the at least one measurand output associated with an x-ray radiation exposure event. In an embodiment, the exposure determination device 122 includes circuitry configured to determine user-specific cumulative exposure information 125 based on the at least one measurand output. Non-limiting examples of cumulative exposure information 124 include cumulative x-ray radiation dose history data, lifetime exposure history data, x-ray radiation exposure alerting protocol data, x-ray radiation exposure response protocol data, x-ray radiation exposure status data, user-specific cumulative x-ray radiation dose history data, user-specific lifetime exposure history data, user-specific x-ray radiation exposure alerting protocol data, user-specific x-ray radiation exposure response protocol data, user-specific x-ray radiation exposure status data, or the like. Further non-limiting examples of cumulative exposure information 124 include depth of x-ray radiation energy deposition data, x-ray radiation energy data, x-ray radiation exposure time data, x-ray radiation intensity data, rate of x-ray radiation energy deposition, or the like.

Further non-limiting examples of cumulative exposure information 124 include absorbed dose data, absorbed dose rate data, committed effective dose data, cumulative dose data, effective dose data, equivalent dose data, exposure data, or the like. Further non-limiting examples of cumulative exposure information 124 include radiation dosimetry conversion data, organ-specific average conversion dose data, organ-specific equivalent conversion dose data, tissue-specific average conversion dose data, tissue-specific equivalent dose conversion data, radiation-type-specific weighting factor data, or the like.

In an embodiment, the exposure determination device 122 includes one or more memory devices 120 and one or more computing devices 116. In an embodiment, the exposure determination device 122 includes one or more memory devices 120 having cumulative exposure information 124 stored thereon. In an embodiment, the exposure determination device 122 includes at least one computing device 116, operably coupled to one or more memory devices 120 having radiation exposure information stored thereon, that assesses, calculates, evaluates, determines, gauges, quantifies, resolves, or the like, cumulative exposure information 124 based on one or more measurand outputs from the radiation sensing device 102. In an embodiment, the exposure determination device 122 includes at least one computing device 116, operably coupled to one or more memory devices 120 having radiation exposure information stored thereon, that generates at least one of radiation intensity data, radiation energy data, radiation exposure time data, rate of radiation energy deposition, or depth of radiation energy deposition data based on one or more measurand outputs from the radiation sensing device 102.

In an embodiment, the exposure determination device 122 includes at least one computing device 116, operably coupled to one or more memory devices 120 having radiation exposure information stored thereon, that generates at least one of absorbed dose data, absorbed dose rate data, committed effective dose data, cumulative dose data, effective dose data, equivalent dose data, or exposure data based on the at least one measurand. In an embodiment, the exposure determination device 122 includes one or more memory devices 120 having International Commission on Radiological Protection (ICRP) weighting factor data stored thereon.

In an embodiment, the exposure determination device 122 includes one or more memory devices 120 having at least one of absorbed dose conversion data, absorbed dose rate conversion data, committed effective dose conversion data, cumulative dose conversion data, effective dose data, equivalent dose conversion data, or exposure conversion data stored thereon. In an embodiment, the exposure determination device 122 includes one or more memory devices 120 having user-specific radiation dosimetry conversion data stored thereon. In an embodiment, the exposure determination device 122 includes one or more memory devices 120 having at least one of organ-specific average conversion dose data, organ-specific equivalent conversion dose data, tissue-specific average conversion dose data, or tissue-specific equivalent dose conversion data stored thereon. In an embodiment, the exposure determination device 122 includes one or more memory devices 120 having radiation-type-specific weighting factor data stored thereon.

In an embodiment, the exposure determination device 122 determines at least one of radiation intensity data, radiation energy data, radiation exposure time data, rate of radiation energy deposition, or depth of radiation energy deposition data based on the at least one measurand output. In an embodiment, the exposure determination device 122 determines at least one of absorbed dose data, absorbed dose rate data, committed effective dose data, cumulative dose data, effective dose data, equivalent dose data, or exposure data based on the at least one measurand output. In an embodiment, the exposure determination device 122 determines at least one weighting factor associated with the type of transcutaneous x-ray radiation stimulus based on the at least one measurand output. In an embodiment, the exposure determination device 122 determines at least one of organ-specific average dose data, organ-specific equivalent dose data, tissue-specific average dose data, or tissue-specific equivalent dose data based on the at least one measurand output. In an embodiment, the exposure determination device 122 determines radiation-type specific weighting factor data based on the at least one measurand output.

In an embodiment, the exposure determination device 122 includes one or more transmitters 126, receivers 127, or transceivers 128. In an embodiment, the exposure determination device 122 includes at least one transmitter 126 or transceiver 128 operable to concurrently or sequentially transmit or receive one or more of cumulative exposure information 124, radiation intensity data, radiation energy data, radiation exposure time data, rate of radiation energy deposition, depth of radiation energy deposition data, absorbed dose data, absorbed dose rate data, committed effective dose data, cumulative dose data, effective dose data, equivalent dose data, or exposure data based on the at least one measurand output.

In an embodiment, the implantable radiation sensing device 102 includes an authorization device 130 that transmits or receives data. For example, in an embodiment, the implantable radiation sensing device 102 includes an authorization device 130 that transmits or receives user-specific data based on at least one of an authorization protocol, an authentication protocol, or an activation protocol. In an embodiment, the authorization device 130 transmits or receives user-specific data based on at least one cryptographic protocol, encryption protocol, or decryption protocol. In an embodiment, the authorization device 130 including speech recognition module that causes the implantable radiation sensing device 102 to change between a transmit states and a receive state using one or, more audio inputs.

In an embodiment, the radiation sensing device 102 includes a biocompatible housing 132 enclosing at least one of the x-ray radiation sensor device 104, or the exposure determination device 122. In an embodiment, the radiation sensing device 102 includes a biocompatible housing 132 having one or more structural elements. Structural elements may be constructed by a variety of manufacturing methods, from a variety of materials. In an embodiment, the biocompatible housing 132 includes one or more structural elements manufactured from metals, ceramics, polymers, or composite materials having suitable biocompatibility, sterilizability, mechanical, or physical properties. In an embodiment the biocompatible housing 132 includes one or more structural elements sized and configured for a particular implantation environment. Non-limiting examples of materials and selection criteria are described, for example, in *The Biomedical Engineering Handbook*, Second Edition, Volume I, J. D. Bronzino, Ed., Copyright 2000, CRC Press LLC, pp. IV-1-43-31.

The biocompatible housing 132 can take a variety of shapes, configurations, and geometries including, for example, cylindrical, conical, planar, parabolic, regular or irregular forms, or the like. In an embodiment, structural elements are formed from one or more biocompatible materials suitable for implantation using a variety of methodologies and technologies. Non-limiting examples of techniques suitable for making the biocompatible housing 132 or structural elements thereof, include injection molding, extrusion, die-cutting, rapid-prototyping, self-assembly, etc. In an embodiment, the biocompatible housing 132 includes one or more biocompatible materials that permit the passage of x-ray radiation from an exterior environment to an interior environment of the biocompatible housing 132. In an embodiment, the biocompatible housing 132 includes one or more biocompatible materials that are at least partially x-ray radiation transparent. In an embodiment, the biocompatible housing 132 includes one or more biocompatible polymers. In an embodiment, the biocompatible housing 132 includes one or more biocompatible plastics.

In an embodiment, one or more of the x-ray radiation sensor device 104, exposure determination device 122, power source 134, in vivo means 202 for generating at least one measurand output indicative of an x-ray radiation exposure event, in vivo means 204 for comparing the measurand output to user-specific radiation exposure information and generating user-specific x-ray radiation exposure information, authorization device, interrogation interface, proposed dose verification device, telematic x-ray radiation exposure reporter 208, x-ray radiation exposure information generator 206, or a power source are received in the interior on the biocompatible housing 132.

In an embodiment, the implantable radiation sensing device 102 includes one or more power sources 134. In an embodiment, the implantable radiation sensing device 102 includes a power source 134 including one or more generators configured to harvest mechanical energy from, for example, acoustic waves, mechanical vibration, blood flow, or the like. For example, in an embodiment, the power source 134 includes at least one of a biological-subject (e.g., human)-powered generator 136, a thermoelectric generator 138, a piezoelectric generator 140, an electromechanical generator (e.g., a microelectromechanical system (MEMS) generator 142, or the like), a biomechanical-energy harvesting generator 144, or the like. In an embodiment, the power source 134 is electromagnetically, magnetically, acoustically, optically, inductively, electrically, or capacitively coupled to at least one of the x-ray radiation sensor device 104, the exposure determination device 122, a computing device 116, a transmitter 126, a receiver 127, a transceiver 128, etc.

Non-limiting examples of power sources 134 examples include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, or the like. Further non-limiting examples of power sources 134 include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, or the like. In an embodiment, the power source 134 includes at least one rechargeable power source. In an embodiment, the power source 134 includes one or more micro-batteries, thin film batteries, fuel cells (e.g., biofuel cells, chemical fuel cells etc), or the like.

In an embodiment, the implantable radiation sensing device 102 carries the power source 134. In an embodiment, the implantable radiation sensing device 102 includes at least one of a battery, a capacitor, or a mechanical energy store (e.g., a spring, a flywheel, or the like). In an embodiment, the implantable radiation sensing device 102 includes a power source 134 including at least one of a battery, a capacitor, or a rechargeable power or a mechanical energy store. In an embodiment, the power source 134 is configured to manage a duty cycle associated with, for example, detecting and quantifying a transcutaneously received x-ray radiation stimulus, in vivo.

In an embodiment, the biological-subject-powered generator 136 is configured to harvest thermal energy generated by the biological subject. In an embodiment, the biological-subject-powered generator 136 is configured to harvest energy generated by the biological subject using at least one of a thermoelectric generator 138, a piezoelectric generator 140, an electromechanical generator 142 (e.g., a microelectromechanical system (MEMS) generator, or the like), a biomechanical-energy harvesting generator 144, or the like. For example, in an embodiment, the biological-subject-powered generator 136 includes one or more thermoelectric generators 138 configured to convert heat dissipated by the biological subject into electricity. In an embodiment, the biological-subject-powered generator 136 is configured to harvest energy generated by any physical motion or movement (e.g., walking, etc.) by a biological subject. For example, in an embodiment, the biological-subject-powered generator 136 is configured to harvest energy generated by the movement of a joint within the biological subject. In an embodiment, the biological-subject-powered generator 136 is configured to harvest energy generated by the movement of a fluid (e.g., biological fluid) within the biological subject.

In an embodiment, the implantable radiation sensing device 102 includes a transcutaneous energy transfer system 146. For example, in an embodiment, the implantable radiation sensing device 102 includes one or more power receivers configured to receive power from at least one of an in vivo or an ex vivo power source. In an embodiment, the transcutaneous energy transfer system 146 is electromagnetically, magnetically, acoustically, optically, inductively, electrically, or capacitively coupled to at least one of the x-ray radiation sensor device 104 the exposure determination device 122, the transmitter 126, the receiver 127, the transceiver 128, or the like. In an embodiment, the transcutaneous energy transfer system 146 is configured to transfer power from at least one of an in vivo or an ex vivo power source to the implantable radiation sensing device 102.

In an embodiment, the transcutaneous energy transfer system 146 is configured to transfer power to the implantable radiation sensing device 102 and to recharge a power source 134 within the implantable radiation sensing device 102. In an embodiment, the transcutaneous energy transfer system 146 is electromagnetically, magnetically, acoustically, optically, inductively, electrically, or capacitively coupleable to an in vivo power supply. In an embodiment, the transcutaneous energy transfer system 146 includes at least one electromagnetically coupleable power supply, magnetically coupleable power supply, acoustically coupleable power supply, optically coupleable power supply, inductively coupleable power supply, electrically coupleable power supply, or capacitively coupleable power supply. In an embodiment, the energy transcutaneous transfer system is configured to wirelessly receive power from a remote power supply.

In an embodiment, while implanted within a biological subject the implantable radiation sensing device 102 communicates with an external x-ray radiation-emitting system 150 (e.g., a medical systems, a cabinet x-ray system, etc.). For example, during operation, the implantable radiation sensing device 102 communicates with an external x-ray radiation-emitting system 150 and acquires proposes dose information (e.g., information regarding x-ray radiation to be deliver by the x-ray radiation-emitting system 150, etc.). Non-limiting examples of external x-ray radiation-emitting systems 150 include airport baggage security screening systems, cargo inspection systems, circuit board inspection systems, communication systems, container scanning systems, food inspection systems, tire inspection systems, or the like. Non-limiting examples of external x-ray radiation-emitting systems 150 include klystron systems, computed tomography systems, fluoroscopy systems, x-ray generation systems, x-ray radiography systems, or the like.

In an embodiment, the implantable radiation sensing device 102 stores proposed dose information in one or more memory structures 120 and utilizes it to, for example, confirm the actual dose received, determine a potential exposure status on a user, generate one or more heuristic associated with a cumulative exposure of a user, or the like.

In an embodiment, the implantable radiation sensing device 102 includes a proposed dose verification device 148. In an embodiment, the proposed dose verification device 148 is configured to transcutaneously elicit proposed dose information, via one or more transmitters 126, receivers 127, or transceivers 128, from an external x-ray radiation-emitting system 150. For example, in an embodiment, the proposed dose verification device 148 is configured to transcutaneously elicit proposed dose information, via one or more transmitters 126, receivers 127, or transceivers 128, from at least one of an airport baggage security screening system, a cargo inspection system, a circuit board inspection system, a communication system, a container scanning system, a food inspection system, or a tire inspection system, a klystron system, a computed tomography system, a fluoroscopy system, an x-ray generation system, an x-ray radiography system, or the like.

In an embodiment, the proposed dose verification device 148 includes one or more transmitters 126, receivers 127, or transceivers 128. For example, in an embodiment, the proposed dose verification device 148 includes at least one of a transmitter 126 or transceiver 128 that concurrently or sequentially transmit or receive one or more of proposed dose information or potential exposure status information. In an embodiment, the proposed dose verification device 148 includes at least one of a transmitter 126 or transceiver 128 operable to detect the external x-ray radiation-emitting system 150. In an embodiment, the proposed dose verification device 148 includes at least one of a transmitter 126, receiver 127, or transceiver 128 operable to wirelessly interface with the external x-ray radiation-emitting system 150.

In an embodiment, the proposed dose verification device 148 includes one or more transmitters 126 or transceivers 128 configured to report status information at regular or irregular time intervals. In an embodiment, the proposed dose verification device 148 includes one or more transmitters 126 or transceivers 128 configured to report status information, proposed dose information, potential exposure status information, etc., at target time intervals. In an embodiment, the proposed dose verification device 148 includes one or more transmitters 126 or transceivers 128 configured to report status information, proposed dose information, potential exposure status information, etc., at a plurality of time intervals and to enter a receive mode for a period after transmitting the report information. In an embodiment, the proposed dose verification device 148 includes one or more transmitters 126 or transceivers 128 configured to report status information, proposed dose information, potential exposure status information, etc., when the relationship between measurands detected at different times exceeds threshold.

In an embodiment, the proposed dose verification device 148 includes one or more transmitters 126 or transceivers 128 configured to report status information, proposed dose information, potential exposure status information, etc., when a relationship between two or more measurands meet or exceed a threshold criterion. In an embodiment, the proposed dose verification device 148 includes one or more transmitters 126 or transceivers 128 to report status information, proposed dose information, potential exposure status information, etc., when a difference between a measurand and a user-related target value exceeds a threshold criterion. In an embodiment, the proposed dose verification device 148 includes at least one of transmitter 126 or transceiver 128 operable to communicate an authorization status to the external x-ray radiation-emitting system 150. In an embodiment, the proposed dose verification device 148 includes at least one of transmitter 126 or transceiver 128 operable to communicate potential exposure status information to the external x-ray radiation-emitting system 150.

In an embodiment, the proposed dose verification device 148 includes an irradiation authorization component 152 that communicates an authorization status to the external x-ray radiation-emitting system 150. In an embodiment, the proposed dose verification device 148 includes an irradiation authorization component 152 that communicates one or more authorization instructions to the external x-ray radiation-emitting system 150 to initiate x-ray radiation delivery. In an embodiment, the proposed dose verification device 148 includes an irradiation authorization component 152 that generates one or more cryptographic keys, based on potential exposure status information, and that provides authorization to the external x-ray radiation-emitting system 150 to initiate x-ray radiation delivery. In an embodiment, the proposed dose verification device 148 includes an irradiation authorization component 152 that generates one or more cryptographic keys and that provides authorized x-ray radiation dose information to the external x-ray radiation-emitting system 150.

In an embodiment, the proposed dose verification device 148 includes at least one transmitter 126 or transceiver 128 operable to communicate modified dose data to the external x-ray radiation-emitting system 150. In an embodiment, the proposed dose verification device 148 includes at least one of transmitter 126 or transceiver 128 operable to communicate modified dose data to the external x-ray radiation-emitting system 150 based on at least one of the proposed dose information or the potential exposure status information. In an embodiment, the proposed dose verification device 148 includes at least one transmitter 126 or transceiver 128 operable to communicate modified dose data to the external x-ray radiation-emitting system 150 based on one or more user-specific criteria.

In an embodiment, the proposed dose verification device 148 includes an x-ray radiation sensor device 104 operable to detect a transcutaneously received x-ray radiation stimulus associated with the external x-ray radiation-emitting system 150. In an embodiment, the proposed dose verification device 148 includes an x-ray radiation sensor device 104 that acquire at least a portion of a transcutaneous x-ray radiation stimulus emitted by the external x-ray radiation-emitting system 150 and transduces the x-ray radiation stimulus acquired by the x-ray radiation sensor device 104 into at least one measurand indicative of an x-ray radiation exposure during an integration period of the x-ray radiation sensor device 104.

In an embodiment, the implantable radiation sensing device 102 includes an exposure determination device 122 that determines a potential exposure status associated with the proposed dose information from the external x-ray radiation-emitting system 150 and generates potential exposure status information. In an embodiment, the implantable radiation sensing device 102 includes a biocompatible housing 132 enclosing the proposed dose verification device 148 and the exposure determination device 122. In an embodiment, the exposure determination device 122 compares the transcutaneously received x-ray radiation stimulus to the proposed dose information and determines actual exposure status information. In an embodiment, the exposure determination device 122 compares the transcutaneously received x-ray radiation stimulus to the proposed dose information and generates actual exposure status information based on the comparison. In an embodiment, the exposure determination device 122 compares the transcutaneously received x-ray radiation stimulus to the proposed dose information and generates cumulative exposure information 124 based on the comparison.

In an embodiment, the exposure determination device 122 includes one or more memory devices 120 having radiation exposure information stored thereon and a computing device 116 that compares the proposed dose information from the external x-ray radiation-emitting system 150 to the radiation exposure information, and generates at least one of proposed absorbed dose data, proposed absorbed dose rate data, proposed committed effective dose data, proposed cumulative dose data, proposed effective dose data, proposed equivalent dose data, or proposed exposure data based on the comparison. In an embodiment, the exposure determination device 122 includes one or more memory devices 120 having radiation exposure information stored thereon and a computing device 116 that compares the proposed dose information from the external x-ray radiation-emitting system 150 to the radiation exposure information, and generates at least one of a potential dose rate potential dose effect, a potential volume of exposure, a potential flux, or a potential total dose. In an embodiment, the exposure determination device 122 includes one or more memory devices 120 having radiation exposure information stored thereon and a computing device 116 that generates one or more parameter inputs for a potential dose deposition model associated with a user.

In an embodiment, the implantable radiation sensing device 102 includes an interrogation-selective interface. For example, in an embodiment, the implantable radiation sensing device 102 includes an interrogation-selective interface operable to provide cumulative potential exposure status information in response to at least one of electromagnetic interrogation or acoustic interrogation of the interrogation-selective interface that satisfies interrogation-selective criteria. In an embodiment, the interrogation-selective interface operably coupled to the exposure determination device 122. In an embodiment, the interrogation-selective criteria includes at least one of a user-specific frequency, a user-specific carrier waveform, implantable radiation sensing device 102 frequency, or an implantable radiation sensing device 102 specific carrier waveform.

Referring to FIG. 1, in an embodiment, a system 100 includes in vivo means 202 for generating at least one measurand output indicative of an x-ray radiation exposure event in response to a transcutaneously received x-ray radiation stimulus. In an embodiment, the in vivo means 202 for generating at least one measurand output indicative of an x-ray radiation exposure event in response to a transcutaneously received x-ray radiation stimulus includes circuitry for generating the at least one measurand output indicative of an x-ray radiation exposure event. For example, in an embodiment, the in vivo means 202 for generating at least one measurand output indicative of an x-ray radiation exposure event includes a computing device 116 operably coupled to at least one of a photodiode array, a scintillator, a thermoluminescent dosimeter, an x-ray radiation fluoroscopic element, or an amorphous silicon thin-film transistor array.

In an embodiment, a system 100 includes in vivo means 204 for comparing the measurand output to user-specific radiation exposure information and generating user-specific x-ray radiation exposure information based on the comparison. In an embodiment, the in vivo means 204 for comparing the measurand output to user-specific radiation exposure information and generating user-specific x-ray radiation exposure information based on the comparison includes circuitry for comparing the measurand output to the user-specific radiation exposure information and for generating user-specific x-ray radiation exposure information. For example, in an embodiment, the in vivo means 204 for comparing the measurand output to the user-specific radiation exposure information and generating the user-specific x-ray radiation exposure information includes one or more memory devices 120 having radiation exposure information stored thereon and a computing device 116 that compares the measurand output indicative of the x-ray radiation exposure event to the radiation exposure information, and generates at least one of radiation intensity data, radiation energy data, radiation exposure time data, rate of radiation energy deposition, or depth of radiation energy deposition data based on the comparison.

In an embodiment, the in vivo means 204 for comparing the measurand output to the user-specific radiation exposure information and generating the user-specific x-ray radiation exposure information includes one or more memory devices 120 having radiation exposure information stored thereon and a computing device 116 that compares the measurand output indicative of the x-ray radiation exposure event to the radiation exposure information, and generates at least one of absorbed dose data, absorbed dose rate data, committed effective dose data, cumulative dose data, effective dose data, equivalent dose data, or exposure data based on the comparison. In an embodiment, the in vivo means 204 for comparing the measurand output to the user-specific radiation exposure information and generating the user-specific x-ray radiation exposure information includes one or more memory devices 120 having radiation exposure information stored thereon and a computing device 116 that compares the measurand output indicative of the x-ray radiation exposure event to the radiation exposure information, and generates cumulative exposure information 124 based on the comparison.

In an embodiment, the system 100 includes a distributed network. Non-limiting examples of distributed networks includes medical enterprise networks (e.g., medical computer networks, medical enterprise networks, out-patient facility networks, hospital networks, doctor office networks, or the like). In an embodiment, the system 100 includes one or more distributed databases connected, for example, via a network. Non-limiting examples of distributed databases include computer searchable databases, relational databases, storage devices, or the like. In an embodiment, a plurality of databases are connected to at least one of a client, a server, a medical enterprise, implantable radiation sensing device 102, or the like, either directly or through a communication network, such as a Local Area Network (LAN), Metropolitan Area Network (MAN), Server Area Network, Small Area Network, Storage Area Network, System Area Network, Wide Area Network (WAN), Wireless Local Area Network (WLAN), or the like.

Figure 2:
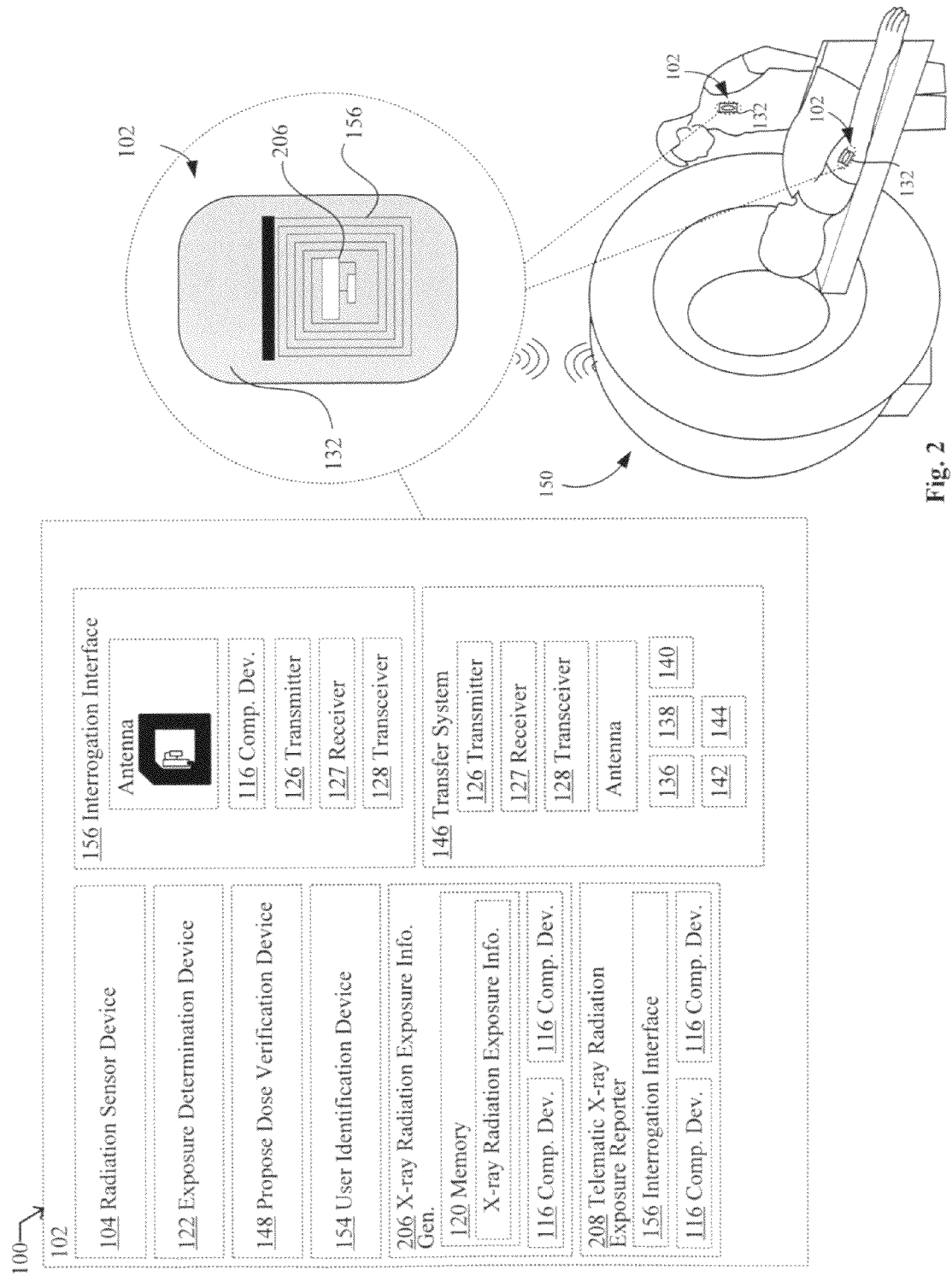
FIG. 2 is a perspective view of a system according to one embodiment.

Referring to FIG. 2, in an embodiment, a system 100 includes an implantable radiation sensing device 102 having a user identification circuit 154 operable to initiate an identification protocol that identifies one of the implantable radiation sensing device 102 or the external x-ray radiation-emitting system 150 and initiates a data transmission protocol between the implantable radiation sensing device 102 and the external x-ray radiation-emitting system 150 based on identification protocol.

In an embodiment, the implantable radiation sensing device 102 includes an interrogation interface 156 operably coupled to the exposure determination device 122, the exposure determination device 122 configured to provide potential exposure status information or cumulative exposure information 124 in response to interrogation of the interrogation interface 156. In an embodiment, the implantable radiation sensing device 102, the interrogation interface 156 is operably coupled to the exposure determination device 122. In an embodiment, the exposure determination device 122 is configured to provide cumulative exposure information 124 in response to interrogation of the interrogation interface 156.

In an embodiment, the implantable radiation sensing device 102 includes at least one transmitter 126 or transceiver 128 operable to concurrently or sequentially transmit or receive cumulative exposure information 124. For example, in an embodiment, the implantable radiation sensing device 102 includes at least one transmitter 126 or transceiver 128 operable to concurrently or sequentially transmit or receive one or more of radiation intensity data, radiation energy data, radiation exposure time data, rate of radiation energy deposition, depth of radiation energy deposition data, absorbed dose data, absorbed dose rate data, committed effective dose data, cumulative dose data, effective dose data, equivalent dose data, or exposure data based on the at least one measurand output.

In an embodiment, a system 100 includes an x-ray radiation exposure information generator 206 including one or more sensors that generate x-ray radiation exposure event information associated with at least one in vivo detected x-ray radiation exposure event. In an embodiment, the x-ray radiation exposure information generator 206 includes one or more memory devices 120 having reference x-ray radiation exposure information stored thereon. In an embodiment, the x-ray radiation exposure information generator 206 includes one or more memory devices 120 having user-specific x-ray radiation exposure information stored thereon. In an embodiment, the x-ray radiation exposure information generator 206 includes at least one computing device 116 operably coupled to one or more memory devices 120 having reference x-ray radiation exposure information stored thereon, the computing device 116 operable to compare the x-ray radiation exposure event information to the reference x-ray radiation exposure information, and to generate cumulative exposure information 124 based on the comparison.

In an embodiment, a system 100 includes a telematic x-ray radiation exposure reporter 208. In an embodiment, telematic x-ray radiation exposure reporter 208 includes one or more interrogation interfaces 156 configured to transcutaneously transmit one or more parameters associated with the x-ray radiation exposure information. In an embodiment, the telematic x-ray radiation exposure reporter 208 transmits a response signal corresponding to at least one of the in vivo detected x-ray radiation exposure event or the x-ray radiation exposure information, responsive to interrogation of the interrogation interface 156 that satisfies response-selective criteria. In an embodiment, the telematic x-ray radiation exposure reporter 208 transmits a response signal corresponding to the x-ray radiation exposure information responsive to interrogation of the interrogation interface 156 that satisfies response-selective criteria.

In an embodiment, the implantable radiation sensing device 102 is configure to communicate with a system 100 (e.g., administration system, billing system, medical system, regulatory compliance system, etc.), a network, a client, a server, or the like, via one or more communication end ports (specified by, for example, an address or a port), communication links, data processing devices, interne systems, mobile communication links, network devices, switched circuit communication links, or the like. Further non-limiting examples of a communication link includes e-mail systems, facsimile (FAX) systems, telephone systems wireless communications systems (e.g., cell phones, personal digital assistant, smart phones, tablet computers systems, etc.), or the like.

FIG. 3A shows an implantable radiation sensing transponder 302. In an embodiment, the implantable radiation sensing transponder 302 includes an x-ray radiation sensor device 104 operable to detect a transcutaneously received x-ray radiation stimulus. In an embodiment, the implantable radiation sensing transponder 302 includes an exposure determination device 122. In an embodiment, the exposure determination device 122 includes one or more memory devices 120 having radiation exposure information stored thereon. In an embodiment, the exposure determination device 122 is configured to record cumulative exposure information 124 based on the transcutaneously received x-ray radiation stimulus.

In an embodiment, the implantable radiation sensing transponder 302 includes an interrogation interface 156. In an embodiment, the interrogation interface 156 is operably coupled to the exposure determination device 122. In an embodiment, the interrogation interface 156 includes an antenna. In an embodiment, the interrogation interface 156 includes at least one bistatic antenna 304. In an embodiment, the interrogation interface 156 includes a carrier waveform selective interrogation interface. In an embodiment, the interrogation interface 156 includes a frequency selective interrogation interface. In an embodiment, the interrogation interface 156 includes an electromagnetic energy selective interrogation interface.

In an embodiment, the interrogation interface 156 is responsive based on at least one of an authorization protocol, an authentication protocol, or an activation protocol. In an embodiment, the exposure determination device 122 and the interrogation interface 156 are operable to emit electromagnetic energy in the radio frequency range. In an embodiment, the exposure determination device 122 and the interrogation interface 156 are operable to emit acoustic energy in the ultrasonic frequency range.

In an embodiment, the exposure determination device 122 is configured to provide cumulative exposure information 124 in response to interrogation of the interrogation interface 156. For example, in an embodiment, the exposure determination device 122 reports cumulative exposure information 124 when the transcutaneously received x-ray radiation stimulus satisfies a threshold criterion. In an embodiment, the exposure determination device 122 reports cumulative exposure information 124 when the transcutaneously received x-ray radiation stimulus meets or exceeds a target range. In an embodiment, the exposure determination device 122 reports cumulative exposure information 124 when the transcutaneously received x-ray radiation stimulus meets or exceeds a threshold value. In an embodiment, the exposure determination device 122 reports cumulative exposure information 124 according to a programmable schedule. In an embodiment, the exposure determination device 122 reports cumulative exposure information 124 subsequent to a transcutaneously received x-ray radiation stimulus event. In an embodiment, the exposure determination device 122 reports cumulative exposure information 124 when report when at least one of a wireless network access point, a Wi-Fi network, or wireless carrier network is detected.

In an embodiment, the exposure determination device 122 includes at least one logic device that compares an output from the x-ray radiation sensor device 104 indicative of the transcutaneously received x-ray radiation stimulus to reference x-ray radiation exposure information, and generates cumulative exposure information 124 based on the comparison.

In an embodiment, the exposure determination device 122 includes at least one logic device that processes an output from the x-ray radiation sensor device 104 indicative of the transcutaneously received x-ray radiation stimulus and generates cumulative exposure information 124 based on the output from the x-ray radiation sensor device 104. For example, in an embodiment, during operation, the exposure determination device 122 includes at least one computing device 116 that processes an output from the x-ray radiation sensor device 104 and generates one or more of organ-specific average dose data, absorbed dose data, absorbed dose rate data, committed effective dose data, cumulative dose data, effective dose data, equivalent dose data, or exposure data. In an embodiment, during operation, the exposure determination device 122 includes at least one computing device 116 that processes an output from the x-ray radiation sensor device 104 and generates cumulative exposure information 124.

In an embodiment, the exposure determination device 122 and the interrogation interface 156 are operable to implement one or more of an amplitude modulation communication protocol, a code-division multiple access communication protocol, a direct-sequence ultra-wideband communication protocol, a frequency division multiple access communication protocol, a frequency modulation communication protocol, an orthogonal frequency division multiple access communication protocol, a time division multiple access communication protocol, an ultra-wideband communication protocol, or a hybrid or combination protocol thereof.

In an embodiment, the exposure determination device 122 includes one or more non-transitory computer-readable memory media including executable instructions stored thereon that, when executed on a computing device 116, instruct the computing device 116 to retrieve from storage one or more parameters associated with the radiation exposure information. In an embodiment, the exposure determination device 122 includes one or more computer-readable memory media including executable instructions stored thereon that, when executed on a computing device 116, instruct the computing device 116 to perform a comparison of output from the x-ray radiation sensor to the one or more parameters associated with the radiation exposure information. In an embodiment, the exposure determination device 122 includes one or more computer-readable memory media including executable instructions stored thereon that, when executed on a computing device 116, instruct the computing device 116 to concurrently or sequentially transmit or receive information associated with the comparison (e.g., in response to the comparison).

In an embodiment, the implantable radiation sensing transponder 302 includes at least one transmit state and at least one receive state. In an embodiment, the implantable radiation sensing transponder 302 toggles between a transmit state and a receive state upon electromagnetic energy interrogation. In an embodiment, the implantable radiation sensing transponder 302 toggles between a transmit state and a receive state upon acoustic energy interrogation.

Figure 3B:
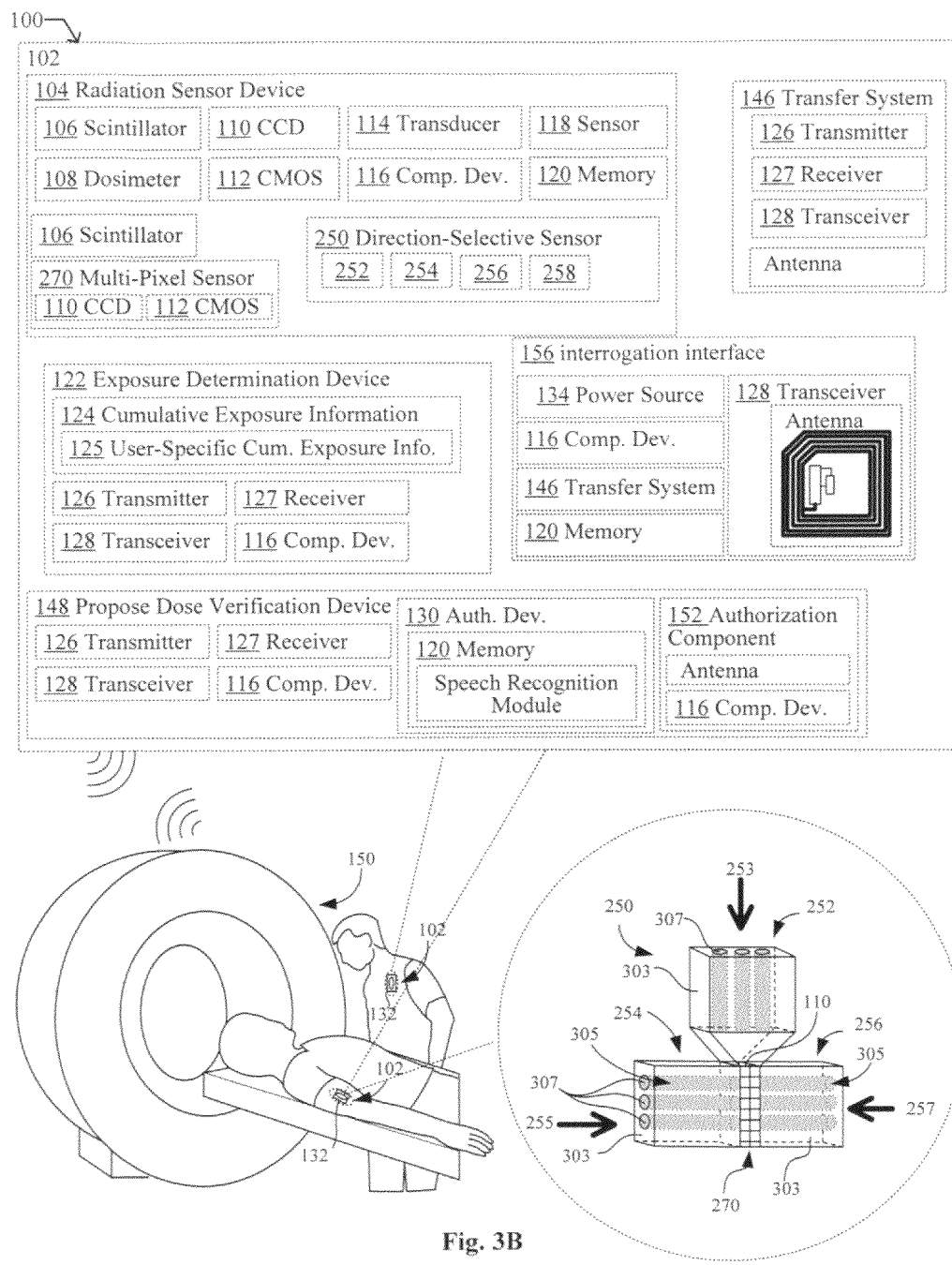
FIG. 3B is a perspective view of a system according to one embodiment.

FIG. 3B shows an implantable radiation sensing device 102, in which one or more methodologies or technologies can be implemented such as, for example, detecting a direction of propagation of an x-ray radiation stimulus. In an embodiment, the implantable radiation sensing device 102 is configured to detect an x-ray radiation stimulus in vivo, monitor lifetime x-ray radiation exposure, assess a radiation exposure status, generate (e.g., calculate, evaluate, determine, gauge, quantify, resolving, or the like) cumulative exposure information, transcutaneously transmit x-ray radiation dose information, receive potential x-ray exposure event information associated with an x-ray radiation-emitting system, determine a potential exposure status of a user, elicit proposed dose information from an x-ray radiation-emitting system or the like.

In an embodiment, the implantable radiation sensing device 102 includes one or more x-ray radiation sensor devices 104 operable to detect, in vivo, one or more x-ray radiation stimuli associated with an x-ray radiation exposure event. For example, during operation, one or more x-ray radiation stimuli (e.g., incident x-ray photons) interact with one or more scintillators 106 of the x-ray radiation sensor devices 104 where they are absorbed and light photons are emitted. In an embodiment the light photons enter one or more waveguides that directed them onto one or more CCDs 110 where they are detected and transduced into one or more electronic measurand outputs.

In an embodiment, the x-ray radiation sensor device 104 includes one or more direction-selective sensors 250. For example, in an embodiment, the x-ray radiation sensor devices 104 include at least a first direction-selective sensor 252 for detecting, in vivo, one or more x-ray radiation stimuli propagating in a first direction 253. In an embodiment, the direction-selective sensor 250 includes a body structure 301 fabricated, doped with, or including one or more materials 303 that limit the passage of x-ray radiation and one or more materials 305 that permit the passage of x-ray radiation 305. Accordingly, an impinging x-ray radiation stimulus propagating in a suitable direction will be acquired by the one or more materials 305 that permit the passage of x-ray radiation and quantified by a corresponding transducer such as a CCD 110 or the like. In an embodiment, impinging x-ray radiation stimuli propagating in a suitable direction will be acquired by the direction-selective sensor 250 and quantified by a corresponding transducer such as a CCD 110 or the like.

In an embodiment, the one or more materials 303 that limit the passage of x-ray radiation comprise one or more ferromagnetic materials. Ferromagnetic materials include those materials having a Curie temperature above which thermal agitation destroys the magnetic coupling giving rise to the alignment of the elementary magnets (electron spins) of adjacent atoms in a lattice (e.g., a crystal lattice). In an embodiment, one or more of the one or more materials 303 that limit the passage of x-ray radiation include one or more ferromagnets. Among ferromagnetic materials, examples include, but are not limited to, crystalline ferromagnetic materials, ferromagnetic oxides, materials having a net magnetic moment, materials having a positive susceptibility to an external magnetic field, non-conductive ferromagnetic materials, non-conductive ferromagnetic oxides, ferromagnetic elements (e.g., cobalt, gadolinium, iron, or the like), rare earth elements, ferromagnetic metals, ferromagnetic transition metals, materials that exhibit magnetic hysteresis, and the like, and alloys or mixtures thereof.

Further examples of ferromagnetic materials include, but are not limited to, chromium (Cr), cobalt (Co), copper (Cu), dysprosium (Dy), europium (Eu), gadolinium (Gd), iron (Fe), magnesium (Mg), neodymium (Nd), nickel (Ni), yttrium (Y), and the like. Further examples of ferromagnetic materials include, but are not limited to, chromium dioxide ($CrO_2$), copper ferrite ($CuOFe_2O_3$), europium oxide (EuO), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), and the like. Further examples of ferromagnetic materials include, but are not limited to, manganese arsenide (MnAs), manganese bismuth (MnBi), manganese(III) antimonide (MnSb), Mn—Zn ferrite, neodymium alloys, neodymium, Ni—Zn ferrite, and samarium-cobalt.

In an embodiment, one or more of the one or more materials 303 that limit the passage of x-ray radiation include at least one iron oxide. Among iron oxides, examples include, but are not limited to, copper ferrite ($CuOFe_2O_3$), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), ferric oxides, ferrous oxides, and the like. In an embodiment, one or more of the one or more materials 303 that limit the passage of x-ray radiation include at least one iron oxide. Among iron oxides, examples include, but are not limited to, copper ferrite ($CuOFe_2O_3$), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), ferric oxides, ferrous oxides, and the like. In an embodiment, one or more of the one or more materials 303 that limit the passage of x-ray radiation are configured to include one or more magnetic components.

In an embodiment, the one or more materials 303 that limit the passage of x-ray radiation comprise one or more ferrimagnetic materials. In an embodiment, one or more of the one or more materials 303 that limit the passage of x-ray radiation include one or more ferrimagnets (e.g., soft ferrites, hard ferrites, or the like). Among ferrimagnetic materials, examples include, but are not limited to, ferrimagnetic oxides (e.g., ferrites, garnets, or the like). Further examples of ferrimagnetic materials include ferrites with a general chemical formula of $AB_2O_4$ (e.g., $CoFe_2O_4$, $MgFe_2O_4$, $ZnFe_2O_4$) where A and B represent various metal cations. In an embodiment, A is Mg, Zn, Mn, Ni, Co, or Fe(II); B is Al, Cr(III), Mn(III) or Fe(III), and O is oxygen. In an embodiment, A is a divalent atom of radius ranging from about 80 pm to about 110 pm (e.g., Cu, Fe, Mg, Mn, Zn, or the like), B is a trivalent atom of radius ranging from about 75 pm to about 90 pm, (e.g., Al, Fe, Co, Ti, or the like), and O is oxygen. Further examples of ferrimagnetic materials include iron ferrites with a general chemical formula $MOFe_2O_3$ (e.g., $CoFe_2O_4$, $Fe_3O_4$, $MgFe_2O_4$, or the like) where M is a divalent ion such as Fe, Co, Cu, Li, Mg, Ni, or Zn.

Further examples of ferromagnetic materials include materials having a magnetization compensation point, materials that are associated with a partial cancellation of antiferromagnetically aligned magnetic sublattices with different values of magnetic moments, or material having different temperature dependencies of magnetization. See e.g., Kageyama et al., Weak Ferrimagnetism, Compensation Point, and Magnetization Reversal in $Ni(HCOO)_2.2H_2O$, Physical Rev. B, 224422 (2003). In an embodiment, the one or more materials 303 that limit the passage of x-ray radiation comprise one or more paramagnetic materials.

In an embodiment, the one or more materials 303 that limit the passage of x-ray radiation comprise at least one of the first x-ray shielding agent or the second x-ray shielding agent and include at least one material that absorbs x-rays at one or more frequencies and fluoresce x-rays at one or more lower frequencies. In an embodiment, at least one of the first x-ray shielding agent or the second x-ray shielding agent includes at least one of boron, molybdenum, neodymium, niobium, strontium, tungsten yttrium, or zirconium, or combinations thereof. In an embodiment, at least one of the first x-ray shielding agent or the second x-ray shielding agent includes at least one of barium sulfate ($BaSO_4$), boron nitride (BN), boron carbide ($B_4C$), boron oxide ($B_2O_3$), or barium oxide (BaO). In an embodiment, at least one of the first x-ray shielding agent or the second x-ray shielding agent includes at least one of strontium oxide (SrO), zinc oxide (ZnO), or zirconium dioxide ($ZrO_2$). In an embodiment, at least one of the first x-ray shielding agent or the second x-ray shielding agent includes one or more $SiO_2$-PbO-alkali metal oxide glasses, CaO—SrO—$B_2O_3$ glasses, or boron-lithium glasses. In an embodiment, at least one of the first x-ray shielding agent or the second x-ray shielding agent includes borated high density polyethylene. In an embodiment, at least one of the first x-ray shielding agent or the second x-ray shielding agent includes at least one of mylar ($C_{10}H_8O_4$), parylene-C ($C_8H_7Cl$), parylene-N($C_8H_8$), poly(methyl methacrylate) (PMMA), polycarbonate ($C_{16}H_{14}O_3$), polyethylene, or ultra high molecular weight polyethylene. In an embodiment, at least one of the first x-ray shielding agent or the second x-ray shielding agent includes silicon nitride ($Si_3N_4$). In an embodiment, at least one of the first x-ray shielding agent or the second x-ray shielding agent includes at least one of mercury (Hg), lead (Pb), lithium fluoride (LiF), tantalum (Ta), or tungsten (W). In an embodiment, at least one of the first x-ray shielding agent or the second x-ray shielding agent includes teflon ($C_2F_4$).

In an embodiment, the direction-selective sensor 250 includes a body structure 301 fabricated, doped with, or including one or more x-ray radio-opaque materials (e.g., barium sulfate, silicon carbide, silicon nitride, alumina, zirconia, etc.); x-ray attenuating materials; x-ray attenuating ceramic materials; high-Z materials (e.g., materials including chemical elements with a high atomic number (Z) of protons in the nucleus, or the like); high density materials or the like. In an embodiment, the direction-selective sensor 250 includes a portion 305 fabricated, doped with, or including one or more materials 307 that permit the passage of x-ray radiation.

In an embodiment, the x-ray radiation sensor devices 104 includes a second direction-selective sensor for detecting, in vivo, one or more x-ray radiation stimuli propagating in a second direction, the second direction 255 different from the first direction 253.

In an embodiment, x-ray radiation sensor device 104 includes a computing device that processes the one or more measurand outputs from at least one of the first direction-selective sensor 252 or the second direction-selective sensor 254 and generates one or more of radiation sensing device geographical location data, device orientation data, or x-ray radiation stimuli propagating direction data associated with the an x-ray radiation exposure event. In an embodiment, x-ray radiation sensor device 104 includes a computing device that processes the one or more measurand outputs from at least one of the first direction-selective sensor 252 or the second direction-selective sensor 254 and generates one or more of time of exposure data, date of exposure data, or exposure duration data associated with the an x-ray radiation exposure event. In an embodiment, x-ray radiation sensor device 104 includes a computing device that processes the one or more measurand outputs from at least one of the first direction-selective sensor 252 or the second direction-selective sensor 254 and generates one or more of intensity data, energy data, rate of energy deposition data, or depth of energy deposition data associated with the an x-ray radiation exposure event. In an embodiment, the x-ray radiation sensor device 104 includes circuitry configured to detect x-ray radiation.

In an embodiment, the x-ray radiation sensor device 104 includes at least one charge-coupled device 110, complementary metal-oxide-semiconductor device 112, or a scintillation detection device. In an embodiment, the x-ray radiation sensor device 104 includes at least one of a photodiode array, a scintillator 106, a thermoluminescent dosimeter, an x-ray radiation fluoroscopic element, or an amorphous silicon thin-film transistor array. In an embodiment, the x-ray radiation sensor device 104 includes at least one computing device operably coupled to one or more sensors 118 configured to acquire at least one of intensity data, phase data, energy, exposure time, rate of energy deposition, or depth of energy deposition associated with the x-ray radiation stimulus.

In an embodiment, the implantable radiation sensing device 102 includes an x-ray radiation direction-determination device 250 operable to determine at least one of an x-ray radiation source location or an x-ray radiation propagation direction based on one or more measurand outputs from at least one of the first direction-selective sensor 252 or the second direction-selective sensor 254. In an embodiment, at least one of the one or more measurand outputs from the first direction-selective sensor 252 or the second direction-selective sensor 254 depends on the x-ray radiation propagation direction relative to orientation of the x-ray radiation sensor device 104.

In an embodiment, the implantable radiation sensing device 102 includes a third direction-selective sensor 256 for detecting, in vivo, one or more x-ray radiation stimuli propagating in a third direction, the third direction 257 different from the second direction 255 and the first direction. In an embodiment, the third direction 257 is orthogonal to at least one of the second direction 255 or the first direction. In an embodiment, the x-ray radiation direction-determination device 250 is operable to determine the x-ray radiation direction by comparing one or more measurand outputs from the first direction-selective sensor 252 and the second direction-selective sensor 254. In an embodiment, the x-ray radiation direction-determination device 250 is operable to determine the x-ray radiation direction by comparing one or more measurand outputs from the first direction-selective sensor 252, the second direction-selective sensor 254, and the third direction-selective sensor 256.

In an embodiment, the x-ray radiation direction-determination device 250 is configured to determine the x-ray radiation direction relative to a coordinate reference external to an implantee. For example, during operation, the x-ray radiation direction-determination device 250 determines a direction of an incident x-ray radiation, in vivo and transforms the direction into a coordinate frame to a body portion of an implantee using one or more transformations. In an embodiment, the x-ray radiation direction-determination device 250 is operable to determine the x-ray radiation direction relative to an x-ray radiation source location emitting the one or more x-ray radiation stimuli. In an embodiment, the first direction-selective sensor 252 and the second direction-selective sensor 254 include one or more pixels that acquire at least a portion of an x-ray radiation stimulus, in vivo, and transduce the x-ray radiation stimulus into at least one measurand indicative of the x-ray radiation exposure event during an integration period of the x-ray radiation sensor device 104.

In an embodiment, the first direction-selective sensor 252 includes one or more directions of propagation selective structures that substantially transmit the x-ray radiation input from the first direction 253 incident while limiting transmission of the x-ray radiation input from the second direction. For example, in an embodiment, the first direction-selective sensor 252 includes at least a first directional antenna and the second direction-selective sensor 254 includes a second directional antenna. In an embodiment, the second directional antenna comprises a different direction characteristic from the first directional antenna. In an embodiment, the second direction-selective sensor 254 includes one or more directions of propagation selective structures that substantially transmit the x-ray radiation input from the second direction 255 incident while limiting transmission of the x-ray radiation input from the first direction. In an embodiment, the second direction 255 is nonparallel to the first direction.

In an embodiment, the x-ray radiation direction-determination device 250 generates one or more cardinal points associated with an x-ray radiation stimulus based on the one or more measurand outputs from at least one of the first direction-selective sensor 252 or the second direction-selective sensor 254. In an embodiment, the x-ray radiation direction-determination device configured to generate one or more position coordinates relative to a coordinate frame associated with the implantable radiation sensing device based on the one or more measurand outputs from at least one of the first direction-selective sensor 252 or the second direction-selective sensor 254.

In an embodiment, the implantable radiation sensing device 102 includes a biocompatible housing 132 enclosing the x-ray radiation sensor device 104. In an embodiment, the biocompatible housing 132 includes one or more biocompatible materials that permit the passage of x-ray radiation from an exterior environment to an interior environment of the biocompatible housing 132. In an embodiment, the biocompatible housing 132 includes one or more biocompatible materials that are at least partially x-ray radiation transparent. In an embodiment, the biocompatible housing 132 includes one or more biocompatible polymers. In an embodiment, the biocompatible housing 132 includes one or more biocompatible plastics.

In an embodiment, the implantable radiation sensing device 102 includes a location sensor 258 for detecting a geographical location associated with the x-ray radiation exposure event. In an embodiment, the implantable radiation sensing device 102 is operable to determine, via at least one global positioning system, a geographical location of the implant during the x-ray radiation exposure event. In an embodiment, the location sensor 258 includes a global positioning system (GPS) receiver. In an embodiment, the location sensor 258 is operable to generate global positioning systems coordinate data associated with the x-ray radiation exposure event. In an embodiment, the location sensor 258 location of device data or orientation of device data based on the one or more measurand outputs from at least one of the first direction-selective sensor 252 or the second direction-selective sensor 254. In an embodiment, the location sensor 258 generates location of exposure event data or orientation of device data based on the one or more measurand outputs from at least one of the first direction-selective sensor 252 or the second direction-selective sensor 254. In an embodiment, the location sensor 258 generates location of exposure event data or orientation of device data associated with a no-implant body location based on the one or more measurand outputs from at least one of the first direction-selective sensor 252 or the second direction-selective sensor 254.

In an embodiment, at least one of the implantable radiation sensing device 102 or the x-ray radiation sensor device 104 includes at least one power source 134 or transcutaneous energy transfer system 146, the transcutaneous energy transfer system electromagnetically, magnetically, ultrasonically, optically, inductively, electrically, or capacitively-coupled to at least one of the x-ray radiation sensor device 104 or the x-ray radiation direction-determination device. In an embodiment, the implantable radiation sensing device 102 includes one or more transmitters 126, receivers 127, or transceiver 128, and is operable to concurrently or sequentially transmit or receive one or more of x-ray radiation source location data or x-ray radiation propagation direction data associated with the x-ray radiation exposure event.

In an embodiment, the implantable radiation sensing device 102 includes an interrogation interface 156 operably coupled to at least one of the x-ray radiation sensor device 104 or the x-ray radiation direction-determination device. In an embodiment, the implantable radiation sensing device 102 is operable to modulate between an ON state and an OFF state responsive to interrogation of the interrogation interface 156 that satisfies response-selective criteria. In an embodiment, the interrogation interface 156 transmits a response signal corresponding to at least one of the x-ray radiation source location or the x-ray radiation propagation direction responsive to interrogation of the interrogation interface that satisfies response-selective criteria.

In an embodiment, an x-ray radiation sensor device 104 includes a multi-pixel x-ray radiation sensor 270 having at least a first pixel and a second pixel, the second pixel having one or more x-ray mass attenuation coefficients different from the first pixel, and the multi-pixel x-ray radiation sensor 270 operable to generate one or more measurand outputs associated with an in vivo detected x-ray radiation exposure event. In an embodiment, the second pixel includes one or more mass energy-absorption coefficients different from the first pixel, and the multi-pixel x-ray radiation sensor 270 is operable to generate one or more measurand outputs associated with an in vivo detected x-ray radiation exposure event.

In an embodiment, an x-ray radiation sensor device 104 includes an exposure determination device 122 that determines exposure information based on the one or more measurand outputs from the multi-pixel x-ray radiation sensor 270. In an embodiment, the second pixel includes one or more absorption edges different from the first pixel. In an embodiment, the second pixel includes one or more characteristic x-ray absorption edges different from the first pixel. In an embodiment, the second pixel includes one or more k-edges or l-edges different from the first pixel. In an embodiment, the second pixel includes at least one k-edge having an energy level lower that at least one k-edge of the first pixel. In an embodiment, the second pixel includes one or more one or more materials having an x-ray absorption edge different from the first pixel. In an embodiment, the second pixel includes one or more one or more layers having materials comprising an x-ray absorption edge different from the first pixel.

In an embodiment, the exposure determination device 122 determines cumulative exposure information based on the one or more measurand outputs from the multi-pixel x-ray radiation sensor 270. In an embodiment, the exposure determination device 122 determines a dose equivalent associated with the in vivo detected x-ray radiation exposure event. In an embodiment, the exposure determination device 122 determines an absorbed dose associated with the in vivo detected x-ray radiation exposure event. In an embodiment, the exposure determination device 122 updates exposure history data based on the one or more measurand outputs from the multi-pixel x-ray radiation sensor 270. In an embodiment, the exposure determination device 122 generates at least one of cumulative x-ray radiation dose history data, lifetime exposure history data, x-ray radiation exposure alerting protocol data, x-ray radiation exposure response protocol data, x-ray radiation exposure status data, user-specific cumulative x-ray radiation dose history data, user-specific lifetime exposure history data, user-specific x-ray radiation exposure alerting protocol data, user-specific x-ray radiation exposure response protocol data, user-specific x-ray radiation exposure status data, or user-specific exposure information based on the one or more measurand outputs from the multi-pixel x-ray radiation sensor 270.

In an embodiment, the exposure determination device 122 includes one or more memory devices 120 having radiation exposure information stored thereon. In an embodiment, the exposure determination device 122 includes at least one transmitter 126, receiver 127, or transceiver 128 configured to receive radiation exposure information. In an embodiment, the exposure determination device 122 includes at least one transmitter 126, receiver 127, transceiver 128 operably coupled to one or more memory devices 120 and configured to receive, and cause the storing onto the one or more memory devices 120 of radiation exposure information. In an embodiment, the exposure determination device 122 includes a computing device 116 that generates at least one of absorbed dose data, absorbed dose rate data, committed effective dose data, cumulative dose data, effective dose data, equivalent dose data, or exposure data based on the one or more measurand outputs.

In an embodiment, the exposure determination device 122 includes one or more memory devices 120 having International Commission on Radiological Protection (ICRP) weighting factor data stored thereon. In an embodiment, the exposure determination device 122 includes one or more memory devices 120 having at least one of absorbed dose conversion data, absorbed dose rate conversion data, committed effective dose conversion data, cumulative dose conversion data, effective dose data, equivalent dose conversion data, or exposure conversion data stored thereon.

In an embodiment, the exposure determination device 122 includes one or more memory devices 120 having user-specific radiation dosimetry conversion data stored thereon. In an embodiment, the exposure determination device 122 includes one or more memory devices 120 having at least one of organ-specific average conversion dose data, organ-specific equivalent conversion dose data, tissue-specific average conversion dose data, or tissue-specific equivalent dose conversion data stored thereon. In an embodiment, the exposure determination device 122 includes one or more memory devices 120 having radiation-type-specific weighting factor data stored thereon.

In an embodiment, the exposure determination device 122 determines at least one of radiation intensity data, radiation energy data, radiation exposure time data, rate of radiation energy deposition, or depth of radiation energy deposition data based on the one or more measurand outputs. In an embodiment, the exposure determination device 122 determines at least one of absorbed dose data, absorbed dose rate data, committed effective dose data, cumulative dose data, effective dose data, equivalent dose data, or exposure data based on the one or more measurand outputs. In an embodiment, the exposure determination device 122 determines at least one weighting factor associated with the type of transcutaneous x-ray radiation stimulus based on the one or more measurand outputs.

In an embodiment, the exposure determination device 122 determines at least one of organ-specific average dose data, organ-specific equivalent dose data, tissue-specific average dose data, or tissue-specific equivalent dose data based on the one or more measurand outputs. In an embodiment, the exposure determination device 122 determines radiation-type specific weighting factor data based on the one or more measurand outputs.

In an embodiment, the multi-pixel x-ray radiation sensor 270 includes one or more scintillators 106. For example in an embodiment, the multi-pixel x-ray radiation sensor 270 includes one or more inorganic scintillators. In an embodiment, the multi-pixel x-ray radiation sensor 270 includes one or more scintillator-photodiode pairs. In an embodiment, the multi-pixel x-ray radiation sensor 270 includes one or more thallium doped cesium iodide scintillators. In an embodiment, the multi-pixel x-ray radiation sensor 270 includes one or more thermoluminescent dosimeters. In an embodiment, the multi-pixel x-ray radiation sensor 270 includes one or more optically stimulated luminescence detectors. In an embodiment, the multi-pixel x-ray radiation sensor 270 includes one or more x-ray radiation fluoroscopic elements. In an embodiment, the multi-pixel x-ray radiation sensor 270 includes one or more phosphorus doped elements.

In an embodiment, the multi-pixel x-ray radiation sensor 270 includes one or more amorphous silicon thin-film transistor arrays. In an embodiment, the multi-pixel x-ray radiation sensor 270 includes one or more phosphors. In an embodiment, the multi-pixel x-ray radiation sensor 270 includes one or more x-ray radiation scintillation crystals. In an embodiment, the multi-pixel x-ray radiation sensor 270 includes one or more thallium doped cesium iodide crystals.

In an embodiment, the multi-pixel x-ray radiation sensor 270 includes one or more photodiode arrays. In an embodiment, the multi-pixel x-ray radiation sensor 270 is configured to output or record pixel-by-pixel exposure information. In an embodiment, the multi-pixel x-ray radiation sensor 270 includes at least one computing device 116 that outputs or causes the recordation of pixel-by-pixel exposure information. In an embodiment, the multi-pixel x-ray radiation sensor 270 is configured to output or record a difference in phase or intensity between at least a first or second pixel.

In an embodiment, an x-ray radiation sensor device 104 includes one or more gel dosimeters operable to detect, in vivo, one or more x-ray radiation stimuli associated with an x-ray radiation exposure event and to generate one or more measurand outputs. In an embodiment, the x-ray radiation sensor device 104 includes one or more computing devices that determine a spatial dose distribution associated with the x-ray radiation exposure event based on the one or more measurand outputs.

In an embodiment, the one or more gel dosimeters include at least one polymer gel dosimeter. Non-limiting examples of gel dosimeter include those found in Jirasek et al., *How Does the Chemistry of Polymer Gel Dosimeters Affect their Performance*? Journal of Physics: Conference Series 164 (2009); Kim B. McAuley, *Fundamentals of Polymer Gel Dosimeters Journal of Physics*, Conference Series 56, pp. 35-44 (2006); and L J Schreiner, *Review of Fricke gel dosimeters*, Journal of Physics: Conference Series, pp. 9-21 (2004); E.B. Podgorsak, Editor, *Radiation Oncology Physics: A Handbook for Teachers and Students*, International Atomic Energy Association, Vienna, Austria, Chapter 3 Radiation Dosimeters, pp. 71-99 (2005); each of which is incorporated herein by reference. In an embodiment, the one or more gel dosimeters include at least one 2-hydroxyethyl-acrylate-based gel dosimeter or 2-hydroxyethyl methacrylate-based gel dosimeter. In an embodiment, the one or more gel dosimeters include at least one polymethacrylic acid-based gel dosimeter or polyacrylamide-based gel dosimeter. In an embodiment, the one or more gel dosimeters include at least one Fricke gel dosimeter. In an embodiment, the one or more gel dosimeters include at least one polyvinyl alcohol-Fricke-based gel dosimeter. In an embodiment, the one or more gel dosimeters include at least one hydrogel-based gel dosimeter or cryogel-based gel dosimeter.

In an embodiment, the implantable radiation sensing device 102 includes an exposure determination device 122 including one or more computing devices 116 that determine at least one of a spatial dose distribution; one-, two- or three-dimensional dose distribution; or an absorbed dose distribution associated with the x-ray radiation exposure event based on the one or more measurand outputs from the x-ray radiation sensor device 122.

Figure 4:
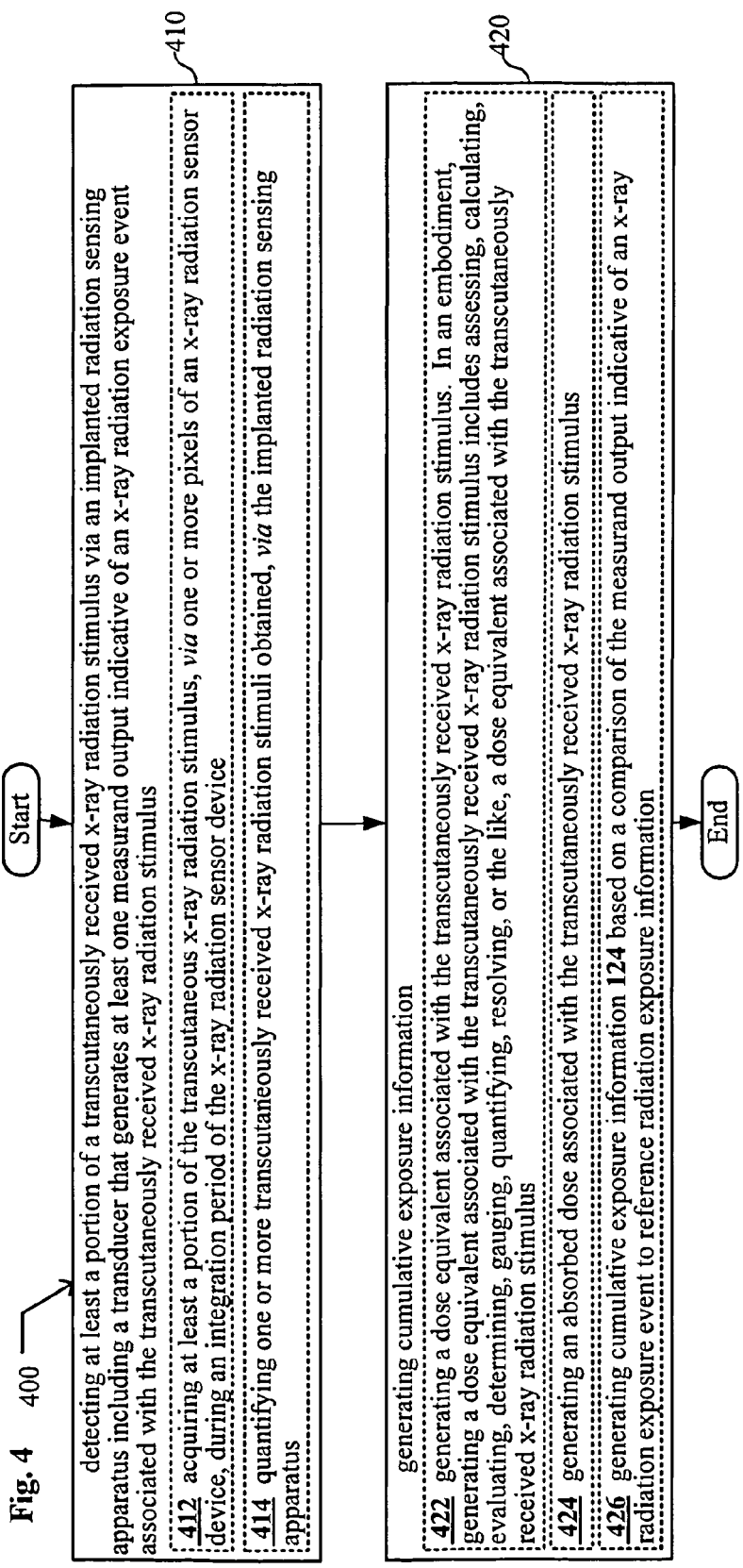
FIG. 4 shows a flow diagram of a method according to one embodiment.

FIG. 4 shows a method 400. At 410, the method 400 includes detecting at least a portion of a transcutaneously received x-ray radiation stimulus via an implanted radiation sensing apparatus including a transducer that generates at least one measurand output indicative of an x-ray radiation exposure event associated with the transcutaneously received x-ray radiation stimulus. At 412, detecting the at least a portion of a transcutaneously received x-ray radiation stimulus via an implanted radiation sensing apparatus includes acquiring at least a portion of the transcutaneous x-ray radiation stimulus, via one or more pixels of an x-ray radiation sensor device 104, during an integration period of the x-ray radiation sensor device 104. At 414, detecting the at least a portion of a transcutaneously received x-ray radiation stimulus via an implanted radiation sensing apparatus includes quantifying one or more transcutaneously received x-ray radiation stimuli obtained, via the implanted radiation sensing apparatus 102.

At 420, the method 400 includes generating cumulative exposure information 124. At 422, generating the cumulative exposure information 124 includes generating a dose equivalent associated with the transcutaneously received x-ray radiation stimulus. In an embodiment, generating a dose equivalent associated with the transcutaneously received x-ray radiation stimulus includes assessing, calculating, evaluating, determining, gauging, quantifying, resolving, or the like, a dose equivalent associated with the transcutaneously received x-ray radiation stimulus. At 424, generating the cumulative exposure information 124 includes generating an absorbed dose associated with the transcutaneously received x-ray radiation stimulus. At 426, generating the cumulative exposure information 124 includes generating cumulative exposure information 124 based on a comparison of the measurand output indicative of an x-ray radiation exposure event to reference radiation exposure information.

Figure 5:
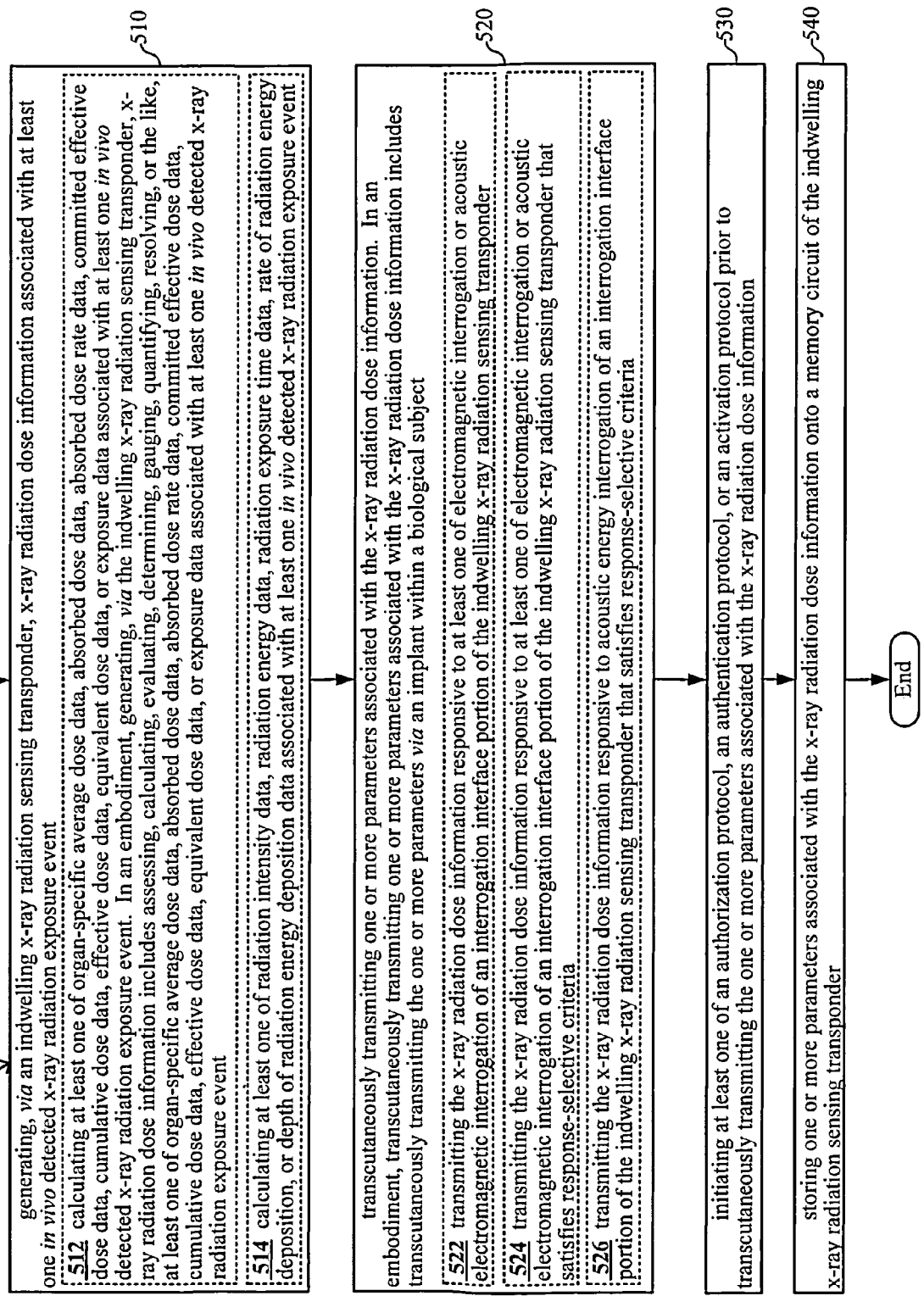
FIG. 5 shows a flow diagram of a method according to one embodiment.

FIG. 5 shows a telematic x-ray radiation monitoring method 500. At 510, the method 500 includes generating, via an indwelling x-ray radiation sensing transponder, x-ray radiation dose information associated with at least one in vivo detected x-ray radiation exposure event. At 512, generating, via the indwelling x-ray radiation sensing transponder, x-ray radiation dose information includes calculating at least one of organ-specific average dose data, absorbed dose data, absorbed dose rate data, committed effective dose data, cumulative dose data, effective dose data, equivalent dose data, or exposure data associated with at least one in vivo detected x-ray radiation exposure event. In an embodiment, generating, via the indwelling x-ray radiation sensing transponder, x-ray radiation dose information includes assessing, calculating, evaluating, determining, gauging, quantifying, resolving, or the like, at least one of organ-specific average dose data, absorbed dose data, absorbed dose rate data, committed effective dose data, cumulative dose data, effective dose data, equivalent dose data, or exposure data associated with at least one in vivo detected x-ray radiation exposure event. At 514, generating, via the indwelling x-ray radiation sensing transponder, x-ray radiation dose information includes calculating at least one of radiation intensity data, radiation energy data, radiation exposure time data, rate of radiation energy deposition, or depth of radiation energy deposition data associated with at least one in vivo detected x-ray radiation exposure event.

At 520, the method 500 includes transcutaneously transmitting one or more parameters associated with the x-ray radiation dose information. In an embodiment, transcutaneously transmitting one or more parameters associated with the x-ray radiation dose information includes transcutaneously transmitting the one or more parameters via an implant within a biological subject. At 522, transcutaneously transmitting the cumulative exposure response includes transmitting the x-ray radiation dose information responsive to at least one of electromagnetic interrogation or acoustic electromagnetic interrogation of an interrogation interface 156 portion of the indwelling x-ray radiation sensing transponder. At 524, transcutaneously transmitting the cumulative exposure response includes transmitting the x-ray radiation dose information responsive to at least one of electromagnetic interrogation or acoustic electromagnetic interrogation of an interrogation interface 156 portion of the indwelling x-ray radiation sensing transponder that satisfies response-selective criteria. At 526, transcutaneously transmitting the cumulative exposure response includes transmitting the x-ray radiation dose information responsive to acoustic energy interrogation of an interrogation interface 156 portion of the indwelling x-ray radiation sensing transponder that satisfies response-selective criteria.

At 530, the method 500 includes initiating at least one of an authorization protocol, an authentication protocol, or an activation protocol prior to transcutaneously transmitting the one or more parameters associated with the x-ray radiation dose information. At 540, the method 500 includes storing one or more parameters associated with the x-ray radiation dose information onto a memory circuit of the indwelling x-ray radiation sensing transponder.

FIG. 6 shows a method 600. At 610, the method 600 includes receiving potential x-ray exposure event information associated with an x-ray radiation-emitting system via an indwelling x-ray radiation sensing transponder. At 612, receiving the potential x-ray exposure event information via an indwelling x-ray radiation sensing transponder includes wirelessly receiving at least one of proposed absorbed dose data, proposed absorbed dose rate data, proposed committed effective dose data, proposed cumulative dose data, proposed effective dose data, proposed equivalent dose data, or proposed exposure data. At 614, receiving the potential x-ray exposure event information via an indwelling x-ray radiation sensing transponder includes wirelessly receiving at least one of a potential dose rate potential dose effect, a potential volume of exposure, a potential flux, or a potential total dose.

At 620, the method 600 includes determining a potential exposure status of a user based on a comparison of the x-ray exposure event information to reference cumulative exposure information. At 630, the method 600 includes storing the potential x-ray exposure event information on one or more memories carried by the indwelling x-ray radiation sensing transponder. At 640, the method 600 includes generating a response based on the potential exposure status. At 642, generating a response includes providing probability of radiation damage information based on the potential exposure status. At 644, generating a response includes providing a radiation exposure status (e.g., no previous radiation exposure, negligible dose of radiation, significant but not a dangerous dose of radiation, significant and dangerous dose of radiation, etc.). At 646, generating the response includes generating at least one of a visual representation, an audio representation, a haptic representation, or a tactile representation indicative of the potential exposure status.

At 650, the method 600 includes detecting at least a portion of a transcutaneously received x-ray radiation stimulus via the indwelling x-ray radiation sensing transponder. At 660, the method 600 includes determining an actual exposure status based on the detected transcutaneously received x-ray radiation stimulus. At 662, determining the potential exposure status of the user includes generating exposure to x-ray radiation information status based on the detected transcutaneously received x-ray radiation stimulus. At 670, the method 600 includes updating cumulative exposure information 124 based on the actual exposure status. At 680, the method 600 includes updating a user on one or more parameters associated with a total past cumulative dose based on the actual exposure status.

FIG. 7 shows a method 700. At 710, the method 700 includes eliciting proposed dose information from an x-ray radiation-emitting system via an indwelling x-ray radiation sensing device. At 712, eliciting the proposed dose information from the x-ray radiation-emitting system via the indwelling x-ray radiation sensing device includes initiating a data transmission transfer between the indwelling x-ray radiation sensing device and the x-ray radiation-emitting system. At 714, eliciting the proposed dose information from the x-ray radiation-emitting system via the indwelling x-ray radiation sensing device includes initiating a data transmission transfer between the indwelling x-ray radiation sensing device and the x-ray radiation-emitting system based on the identification of the x-ray radiation sensing device 102. At 720, the method 700 includes determining a potential exposure status of a user in response to one or more transcutaneously received signals associated with the elicited proposed dose information.

At 730, the method 700 includes generating at least one of a visual representation, an audio representation, a haptic representation, or a tactile representation indicative of the potential exposure status of the user. In an embodiment, the method 700 includes providing a user-specific radiation treatment regimen based on the actual exposure status of the user. In an embodiment, the method 700 generating the response includes initiating a radiation treatment protocol based on the actual exposure status of the user. At 740, the method 700 includes updating a stored radiation treatment protocol based on the potential exposure status of the user. At 745, the method 700 includes determining an actual exposure status of the user based on a comparison of an in vivo detected x-ray radiation measurand from the indwelling implant to the proposed dose information. At 750, the method 700 includes generating a modification to a treatment protocol based at least in part on the actual exposure status. At 755, the method 700 includes generating at least one of a visual representation, an audio representation, a haptic representation, or a tactile representation indicative of the actual exposure status of the user. At 760, the method 700 includes updating cumulative exposure information 124 based on the actual exposure status. At 765, the method 700 includes modifying a user-specific radiation treatment regimen based on the actual exposure status of the user. At 770, the method 700 includes initiating a radiation treatment protocol based on the actual exposure status of the user.

FIGS. 8A and 8B show a method 800 of assessing a radiation exposure status. At 810, the method 800 includes determining an exposure status of a user in response to one or more transcutaneously received x-ray radiation stimuli obtained via an implanted radiation sensing apparatus. At 812, determining the exposure status includes generating one or more of intensity data, energy data, exposure time data, rate of energy deposition data, or depth of energy deposition data associated with the one or more transcutaneously received x-ray radiation stimuli. At 814, determining the exposure status includes comparing a measurand output from the implanted radiation sensing apparatus indicative of the one or more transcutaneously received x-ray radiation stimuli to cumulative exposure information 124, and determining an exposure status of the user based on the comparison.

At 816, determining the exposure status includes comparing a measurand output from the implanted radiation sensing apparatus indicative of the one or more transcutaneously received x-ray radiation stimuli to at least one of organ-specific average conversion dose data, organ-specific equivalent conversion dose data, tissue-specific average conversion dose data, or tissue-specific equivalent dose conversion data, and determining an exposure status of the user based on the comparison. At 818, determining the exposure status includes comparing a measurand output from the implanted radiation sensing apparatus indicative of the one or more transcutaneously received x-ray radiation stimuli to radiation-type-specific weighting factor data, and determining an exposure status of the user based on the comparison. At 820, determining the exposure status includes comparing a measurand output from the implanted radiation sensing apparatus indicative of the one or more transcutaneously received x-ray radiation stimuli to at least one of organ-specific average conversion dose data, absorbed dose conversion data, absorbed dose rate conversion data, committed effective dose conversion data, cumulative dose conversion data, effective dose data, equivalent dose conversion data, or exposure conversion data, and determining an exposure status of the user based on the comparison.

At 822, determining the exposure status includes comparing a measurand output from the implanted radiation sensing apparatus indicative of the one or more transcutaneously received x-ray radiation stimuli to International Commission on Radiological Protection (ICRP) weighting factor data, and determining an exposure status of the user based on the comparison. At 824, determining the exposure status includes comparing a measurand output from the implanted radiation sensing apparatus indicative of the one or more transcutaneously received x-ray radiation stimuli to user-specific radiation dosimetry conversion data, and determining an exposure status of the user based on the comparison.

At 830, the method 800 includes generating a response indicative of an x-ray radiation exposure status. At 832, generating the response indicative of an x-ray radiation exposure status includes generating an output indicative of a current cumulative x-ray radiation dose history. At 834, generating the response indicative of an x-ray radiation exposure status includes generating an output indicative of a current user-specific lifetime exposure history. At 836, generating the response indicative of an x-ray radiation exposure status includes generating an output indicative of a current x-ray radiation exposure status. At 838, generating the response indicative of an x-ray radiation exposure status includes generating at least one of a visual representation, an audio representation, a haptic representation, or a tactile representation indicative of an x-ray radiation exposure status.

At 840, generating the response indicative of an x-ray radiation exposure status includes generating at least one of a visual representation, an audio representation, a haptic representation, or a tactile representation indicative of at least one of an x-ray radiation exposure response protocol or an x-ray radiation exposure alerting protocol. At 850, the method 800 includes updating a user-specific lifetime exposure history based on the response indicative of an x-ray radiation exposure status. At 860, the method 800 includes updating a cumulative x-ray radiation dose history based on the response indicative of an x-ray radiation exposure status.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system can be implemented utilizing suitable commercially available components, such as those typically found in data computing/communication and/or network computing/communication systems.

In an embodiment, a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., t transmitter 126, receiver 127, transceiver 128, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An implantable radiation sensing device, comprising:
an x-ray radiation sensor device operable to detect, in vivo, one or more x-ray radiation stimuli associated with an x-ray radiation exposure event, the x-ray radiation sensor device including at least a first direction-selective sensor for detecting, in vivo, one or more x-ray radiation stimuli propagating in a first direction, and a second direction-selective sensor for detecting, in vivo, one or more x-ray radiation stimuli propagating in a second direction, the second direction different from the first direction; and
an x-ray radiation direction-determination device operable to determine at least one of an x-ray radiation source location or an x-ray radiation propagation direction based on one or more measurand outputs from at least one of the first direction-selective sensor or the second direction-selective sensor.

2. The implantable radiation sensing device of claim 1, further comprising:
a third direction-selective sensor for detecting, in vivo, one or more x-ray radiation stimuli propagating in a third direction, the third direction different from the second direction and the first direction.

3. The implantable radiation sensing device of claim 1, wherein the first direction-selective sensor and the second direction-selective sensor include one or more pixels that acquire at least a portion of an x-ray radiation stimulus, in vivo, and transduce the x-ray radiation stimulus into at least one measurand indicative of the x-ray radiation exposure event during an integration period of the x-ray radiation sensor device.

4. The implantable radiation sensing device of claim 1, wherein the first direction-selective sensor includes one or more directions of propagation selective structures that substantially transmits the x-ray radiation input from the first direction incident while limiting transmission of the x-ray radiation input from the second direction.

5. The implantable radiation sensing device of claim 1, wherein the x-ray radiation direction-determination device generates one or more position coordinates relative to a coordinate frame associated with the implantable radiation sensing device based on the one or more measurand outputs from at least one of the first direction-selective sensor or the second direction-selective sensor.

6. The implantable radiation sensing device of claim 1, further comprising:
a biocompatible housing enclosing the x-ray radiation sensor device.

7. The implantable radiation sensing device of claim 6, wherein the biocompatible housing includes one or more biocompatible materials that permit the passage of x-ray radiation from an exterior environment to an interior environment of the biocompatible housing.

8. The implantable radiation sensing device of claim 1, further comprising:
a location sensor for detecting a geographical location associated with the x-ray radiation exposure event.

9. The implantable radiation sensing device of claim 8, wherein the location sensor generates location of device data or orientation of device data based on the one or more measurand outputs from at least one of the first direction-selective sensor or the second direction-selective sensor.

10. The implantable radiation sensing device of claim 1, wherein the x-ray radiation sensor device includes at least one computing device operably coupled to one or more sensors configured to acquire at least one of intensity data, energy, exposure time, rate of energy deposition, or depth of energy deposition associated with the x-ray radiation stimulus.

11. The implantable radiation sensing device of claim 1, further comprising:
a power source, the power source including at least one of a thermoelectric generator, a piezoelectric generator, a microelectromechanical system generator, or a biomechanical-energy harvesting generator.

12. The implantable radiation sensing device of claim 1, further comprising:
an interrogation interface operably coupled to at least one of the x-ray radiation sensor device or the x-ray radiation direction-determination device.

13. The implantable radiation sensing device of claim 1, further comprising:
at least one of receiver, transmitter, or transceiver configured to communicate radiation exposure information with a network.

14. The implantable radiation sensing device of claim 13, wherein the network includes at least one of an enterprise network, a medical enterprise network, a body area network, or a wireless area network.

15. An x-ray radiation sensor device, comprising:
a multi-pixel x-ray radiation sensor having at least a first pixel and a second pixel, the second pixel having one or more x-ray mass attenuation coefficients different from the first pixel, the multi-pixel x-ray radiation sensor operable to generate one or more measurand outputs associated with an in vivo detected x-ray radiation exposure event; and
an exposure determination device that determines exposure information based on the one or more measurand outputs from the multi-pixel x-ray radiation sensor.

16. The x-ray radiation sensor device of claim 15, wherein the second pixel includes one or more characteristic x-ray absorption edges different from the first pixel.

17. The x-ray radiation sensor device of claim 15, wherein the exposure determination device generates at least one of cumulative x-ray radiation dose history data, lifetime exposure history data, x-ray radiation exposure alerting protocol data, x-ray radiation exposure response protocol data, x-ray radiation exposure status data, user-specific cumulative x-ray radiation dose history data, user-specific lifetime exposure history data, user-specific x-ray radiation exposure alerting protocol data, user-specific x-ray radiation exposure response protocol data, user-specific x-ray radiation exposure status data, or user-specific exposure information based on the one or more measurand outputs from the multi-pixel x-ray radiation sensor.

18. The x-ray radiation sensor device of claim 15, wherein the exposure determination device includes one or more memory devices having radiation exposure information stored thereon.

19. The x-ray radiation sensor device of claim 15, wherein the exposure determination device includes at least one of receiver, transmitter, or transceiver configured to receive radiation exposure information.

20. The x-ray radiation sensor device of claim 15, wherein the exposure determination device includes one or more memory devices having at least one of absorbed dose conversion data, absorbed dose rate conversion data, committed effective dose conversion data, cumulative dose conversion data, effective dose data, equivalent dose conversion data, or exposure conversion data stored thereon.

21. The x-ray radiation sensor device of claim 15, wherein the exposure determination device includes one or more memory devices having user-specific radiation dosimetry conversion data stored thereon.

22. The x-ray radiation sensor device of claim 15, wherein the multi-pixel x-ray radiation sensor includes one or more scintillators.

23. The x-ray radiation sensor device of claim 15, wherein the multi-pixel x-ray radiation sensor includes one or more thermoluminescent dosimeters.

24. The x-ray radiation sensor device of claim 15, wherein the multi-pixel x-ray radiation sensor includes one or more x-ray radiation scintillation crystals.

25. The x-ray radiation sensor device of claim 15, wherein the multi-pixel x-ray radiation sensor is configured to output or record pixel-by-pixel exposure information.

26. The x-ray radiation sensor device of claim 15, wherein the multi-pixel x-ray radiation sensor includes at least one computing device that outputs or causes the recordation of pixel-by-pixel exposure information.

27. The x-ray radiation sensor device of claim 15, wherein the multi-pixel x-ray radiation sensor is configured to output or record a difference in phase or intensity between at least a first pixel or a second pixel.

28. An implantable radiation sensing device, comprising:
an x-ray radiation sensor device operable to detect, in vivo, one or more x-ray radiation stimuli associated with an x-ray radiation exposure event and to generate one or more measurand outputs, the x-ray radiation sensor device including one or more gel dosimeters; and
an exposure determination device including one or more computing devices that determine a spatial dose distribution associated with the x-ray radiation exposure event based on the one or more measurand outputs from the x-ray radiation sensor device.

29. The implantable radiation sensing device of claim 28, wherein the one or more gel dosimeters include at least one polymer gel dosimeter.

30. The implantable radiation sensing device of claim 28, wherein the one or more gel dosimeters include at least one Fricke gel dosimeter.

31. The implantable radiation sensing device of claim 28, wherein the one or more gel dosimeters include at least one hydrogel-based gel dosimeter or cryogel-based gel dosimeter.

* * * * *